United States Patent
Yamakawa et al.

(10) Patent No.: US 8,837,666 B2
(45) Date of Patent: Sep. 16, 2014

(54) X-RAY CT APPARATUS

(75) Inventors: Keisuke Yamakawa, Kokubunji (JP); Yasutaka Konno, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 774 days.

(21) Appl. No.: 13/054,476

(22) PCT Filed: Jul. 24, 2009

(86) PCT No.: PCT/JP2009/063285
§ 371 (c)(1),
(2), (4) Date: Jan. 14, 2011

(87) PCT Pub. No.: WO2010/038536
PCT Pub. Date: Apr. 8, 2010

(65) Prior Publication Data
US 2011/0116594 A1    May 19, 2011

(30) Foreign Application Priority Data

Sep. 30, 2008   (JP) .................. 2008-254973

(51) Int. Cl.
*A61B 6/03*      (2006.01)
*G06T 5/00*      (2006.01)
*A61B 6/00*      (2006.01)

(52) U.S. Cl.
CPC ....... *A61B 6/032* (2013.01); *G06T 2207/20192* (2013.01); *G06T 2207/20104* (2013.01); *G06T 2207/30004* (2013.01); *G06T 5/002* (2013.01); *G06T 2207/20012* (2013.01); *A61B 6/542* (2013.01); *A61B 6/482* (2013.01); *G06T 2207/10081* (2013.01)
USPC ........................................... 378/19; 382/131

(58) Field of Classification Search
CPC ........ A61B 6/03; A61B 6/032; A61B 6/5258; A61B 6/5205; G06T 5/002; G06T 2207/20012; G06T 2207/20032; G06T 2207/20004; G06T 5/001; G06K 9/40
USPC ........................................................ 382/131
See application file for complete search history.

(56) References Cited

U.S. PATENT DOCUMENTS

| 6,493,416 | B1 | 12/2002 | Hsieh |
| 2003/0071220 | A1* | 4/2003 | Bruder et al. ................. 250/369 |
| 2007/0248255 | A1* | 10/2007 | Chen ............................. 382/131 |

FOREIGN PATENT DOCUMENTS

| JP | 7-136157 | 5/1995 |
| JP | 10-43177 | 2/1998 |

(Continued)

OTHER PUBLICATIONS

PTO 12-2763 which is an english translation of JP 2002-153454A.*

(Continued)

*Primary Examiner* — Toan Ton
*Assistant Examiner* — John Corbett
(74) *Attorney, Agent, or Firm* — Brundidge & Stanger, P.C.

(57) ABSTRACT

Smoothing processing appropriate for a subject is performed and a CT image in which artifacts are reduced is acquired. At least a part of the X-ray detecting data 171 and the projection data 174 is used to generate boundary data 175, and at least one of the X-ray detecting data and the projection data is subjected to smoothing processing, by using the boundary data as a threshold. With this configuration, it is possible to perform smoothing processing by using as the threshold, the boundary data generated from the X-ray detecting data that passed through the subject or its projection data, enabling the smoothing processing adapted to the subject, and accordingly, the artifacts are removed while suppressing deterioration of spatial resolution.

15 Claims, 18 Drawing Sheets

(56) References Cited

FOREIGN PATENT DOCUMENTS

| | | |
|---|---|---|
| JP | 2002-153454 | 5/2002 |
| JP | 2003-180675 | 7/2003 |
| JP | 2005-6832 | 1/2005 |
| JP | 2005323926 | 11/2005 |

OTHER PUBLICATIONS

Barrett et al., Artifact in CT: Recognition and Avoidance, 2004, Radiographics, vol. 24, pp. 1679-1691.*

* cited by examiner

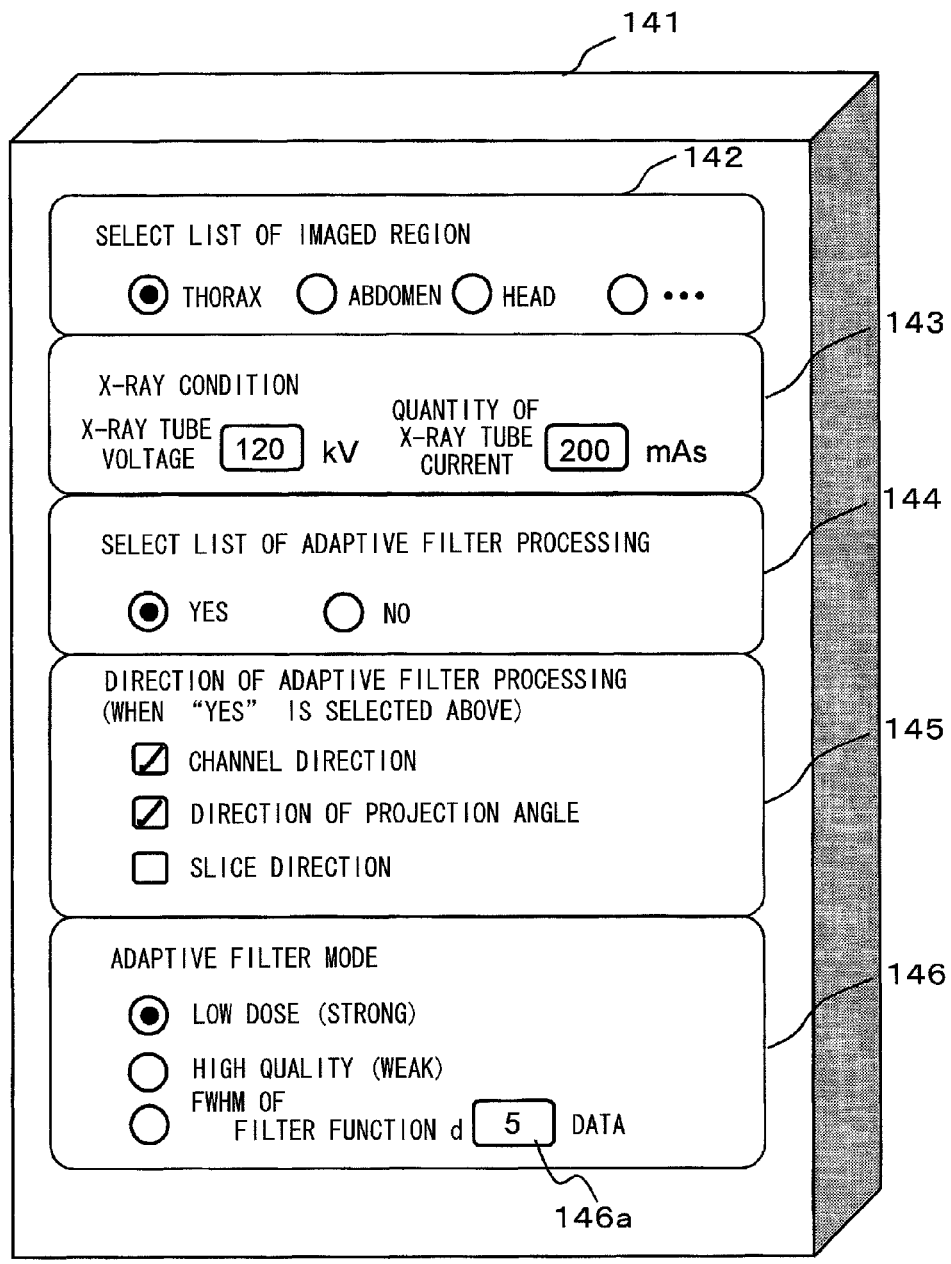
F I G. 3

X-RAY CT APPARATUS

TECHNICAL FIELD

The proposed method relates to an X-ray CT (Computed Tomography) apparatus, and more particularly, it relates to a technique which uses an adaptive filter to smooth data acquired at the time of imaging, and reduces artifacts in a CT image.

BACKGROUND ART

The X-ray CT apparatus calculates an X-ray attenuation coefficient of each point from X-ray projection data which is obtained by multidirectional imaging of a subject, and acquires a computed tomographic image (hereinafter, referred to as "CT image") of the subject. The CT image acquired by this apparatus allows an accurate and immediate diagnosis of a medical condition of a patient at a medical site, and it is clinically useful. However, in order to acquire an image with a high image quality necessary for a doctor to make a diagnosis, a certain amount of radiation exposure is inevitable. In recent years, an influence on the human body exerted by the radiation exposure is perceived as a problem, and there are growing needs for lower exposure. However, as a dose of radiation is lowered to achieve the lower exposure, resulting in decrease of the ratio of signal strength to noise (hereinafter, referred to as "S/N ratio"), and a linear artifact (hereinafter, referred to as "streak artifact") may occur which causes erroneous diagnosis.

On the other hand, in some cases, the streak artifact may occur due to the subject to be imaged. For example, in such a case that normal-dose imaging is performed on the subject's thorax or abdomen under the condition that both arms come into contact with his or her sides, much X-rays is attenuated in the direction connecting the both arms, resulting in a decrease of signal amount. Therefore, the S/N ratio is decreased and occurrence of the streak artifact is inevitable. This causes a problem that it is not possible to obtain an image with a favorable image quality.

In order to solve the problem above, for example, the patent document 1 and the patent document 2 suggest an adaptive filter. This filter performs smoothing processing on projection data acquired at the time of imaging, and reduces noise that is a primary cause of the artifacts. The patent document 1 discloses a technique that X-ray detecting data is homogeneously smoothed for each channel to reduce the artifacts. The patent document 2 discloses a technique that uses a noise distribution σ approximated from projection data and smoothes the projection data according to a weight of the filter, which is calculated for each channel.

PRIOR ART DOCUMENTS

Patent Documents

Patent document 1: Japanese Unexamined Patent Application Publication No. 2005-253628
Patent document 2: Japanese Unexamined Patent Application Publication No. 2003-180675

SUMMARY OF THE INVENTION

Problem to be Solved by the Invention

In the conventional technique, the same filter condition is used for projection data of all the channels, irrespective of the subject, and therefore, there is a possibility that excessive effect of the smoothing deteriorates spatial resolution, or the artifacts still reside due to ineffective smoothing. There is another problem that a large calculation amount and memory amount are needed, since the conventional technique performs calculation for all the channels.

An object of the proposed method is to acquire a CT image in which artifacts are reduced by smoothing processing that is appropriate for the subject.

Means to Solve the Problem

In order to achieve the above object, the X-ray CT apparatus as described below is provided according to the proposed method. In other words, the X-ray CT apparatus of the proposed method includes, an X-ray irradiation unit for irradiating X-rays, an X-ray detecting unit for detecting the X-rays that have passed through a subject and generating X-ray detecting data, a calculation unit of projection data for subjecting the X-ray detecting data to logarithmic conversion and generating projection data, a filter processing unit for smoothing at least one of the X-ray detecting data and the projection data, and an image calculation unit for calculating from the projection data acquired in the filter processing unit, a CT image which represents a distribution of X-ray attenuation coefficient. The filter processing unit generates boundary data by using at least a part of the X-ray detecting data and the projection data, and performs the smoothing processing on at least one of the X-ray detecting data and the projection data, using the boundary data as a threshold. As thus described, since the smoothing processing is performed using as the threshold, the boundary data generated from the X-ray detecting data which passed through the subject or the projection data generated therefrom, the smoothing processing adapted to the subject can be executed, thereby removing the artifacts while suppressing deterioration of spatial resolution.

By way of example, the filter processing unit has a configuration that compares the X-ray detecting data with the boundary data, or the projection data with the boundary data, and switches a degree of smoothing according to magnitude relation between the compared data. Specifically, it is configured such that a comparison is made between the projection data and the boundary data, and the smoothing processing is not performed in an area where the projection data is smaller than the boundary data, whereas in the area where the projection data is equal to or larger than the boundary data, the smoothing processing is performed in accordance with a difference between the projection data and the boundary data. Alternatively, it is configured such that a comparison is made between the X-ray detecting data and the boundary data, and the smoothing processing is not performed in an area where the X-ray detecting data is larger than the boundary data, whereas in the area where the X-ray detecting data is equal to or smaller than the boundary data, the smoothing processing is performed in accordance with a difference between the X-ray detecting data and the boundary data. Further alternatively, it is configured such that upper boundary data and lower boundary data are set, and in an area having equal to smaller than the upper boundary data, or equal to or larger than the lower boundary data, the smoothing processing is performed in accordance with a difference between the projection data and the boundary data, or a difference between the X-ray detecting data and the boundary data. As thus described, the degree of the smoothing is switched according to the magnitude relation between the X-ray detecting data and the boundary data, or between the projection data and the boundary data. With this configuration, a noise component can be strongly smoothed, and simultaneously, for a component other than the noise, deterioration of the spatial resolution caused by the smoothing can be suppressed.

The filter processing unit generates the boundary data by performing the smoothing processing on the X-ray detecting data or the projection data. Accordingly, it is possible to generate the boundary data adapted to characteristic of the subject, and therefore, according to a threshold processing using this boundary data, it is possible to distinguish the noise component from the component other than the noise with a high degree of precision.

On this occasion, in the case where the boundary data is generated from the X-ray detecting data, the area equal to or smaller than a predetermined threshold is assumed as a filter application range and the boundary data can be generated by subjecting the X-ray detecting data within the filter application range to the smoothing processing. Since the area where the X-ray detecting data is smaller than the threshold is apt to contain noises, the boundary data is generated assuming this area as the filter application range, thereby effectively smoothing the area which is more likely to have noises, and suppressing the artifacts. Since the smoothing processing is not performed on the area outside the filter application range, deterioration of spatial resolution can be suppressed as well as reducing a calculation amount and a memory amount. When the boundary data is generated from the projection data, the area equal to or larger than a predetermined threshold is assumed as the filter application range and the smoothing processing is performed on the projection data within the filter application range. Accordingly, similar effect can be obtained.

Two or more types of data are available as boundary data. By way of example, as for the X-ray detecting data, the smoothing processing is performed on the X-ray detecting data in the area equal to or smaller than a predetermined first threshold, and thereafter the data is subjected to logarithmic conversion to generate the first boundary data. As for the projection data, the smoothing processing is performed on the projection data in the area equal to or larger than a predetermined second threshold, thereby generating the second boundary data. It is possible to perform the smoothing processing on the projection data, by selectively using either one of the first boundary data and the second boundary data. When the selection is made, a variation rate of the first boundary data and a variation rate of the second boundary data are obtained, and the data having a smaller variation rate can be selected.

When two or more types of boundary data are used, the variation rate is obtained with respect to each channel direction, and it is possible to select for each channel, either the first boundary data or the second boundary data.

It is further possible to perform the smoothing processing on the X-ray detecting data in a first area of the X-ray detecting data, being equal to or less than a predetermined first threshold, and thereafter performs logarithmic conversion thereon so as to generate the first boundary data, performs the smoothing processing on the projection data in a second area of the projection data, being outside the first area and equal to or more than a predetermined second threshold so as to generate the second boundary data, and performs the smoothing processing on the projection data, by using the first boundary data for the first area and by using the second boundary data for the second area. On this occasion, it is desirable to configure the first threshold and the second threshold in such a manner that the first area becomes an area where the X-ray dose after passing through the subject is lower than the dose in the second area. With this configuration, the smoothing processing is performed, using the first boundary data for the area including a low X-ray dose and the largest amount of noises, whereas using the second boundary data for the area, outside the first area, including less noise.

It is further possible to configure such that the CT apparatus of the proposed method has a noise detecting unit for detecting a noise value of a CT image. When the noise value detected by the noise detecting unit is larger than a predetermined value, the filter processing unit changes conditions of the smoothing processing, thereby reducing noises. For example, the filter processing unit changes the condition of smoothing processing by changing a value of the boundary data.

It is further possible to configure the CT apparatus of the proposed method such that artifacts are estimated before imaging. By way of example, the CT apparatus may further include an input unit for accepting an X-ray irradiation condition of the X-ray irradiation unit, a processing condition of the filter processing unit, and a region of the subject, a storage unit for storing a residual amount of artifact which is obtained in advance with respect to each of the X-ray irradiation condition, the processing condition of the filter processing unit, and the region of the subject, and an artifact estimation unit for reading from the storage unit, the residual amount of artifact in association with information of the X-ray irradiation condition, the processing condition of the filter processing unit, and the subject region, the information being accepted by the input unit. In the case where the residual amount of artifact is larger than a predetermined value, the artifact estimation unit sends a notice to an operator. Accordingly, the operator is allowed to know the residual amount of artifact in advance, which is estimated prior to imaging, whereby the operator is informed of appropriate X-ray irradiation condition, filter processing condition, and the like. It is further possible to configure such that if the residual amount of artifact is larger than the predetermined value, the filter processing unit automatically changes the condition of smoothing processing.

Effect of the Invention

According to the proposed method, it is possible to reduce artifacts which are apt to occur frequently in the imaging with a low dose. Therefore, low dose imaging becomes implementable.

BRIEF DESCRIPTION OF DRAWINGS

FIG. 3 illustrates a monitor screen 141 for setting imaging condition of the input unit of imaging condition 101 in the first embodiment;

BEST MODE FOR CARRYING OUT THE INVENTION

Hereinafter, preferred embodiments of the proposed method will be explained in detail with reference to the accompanying drawings.

First Embodiment

Figure 1:
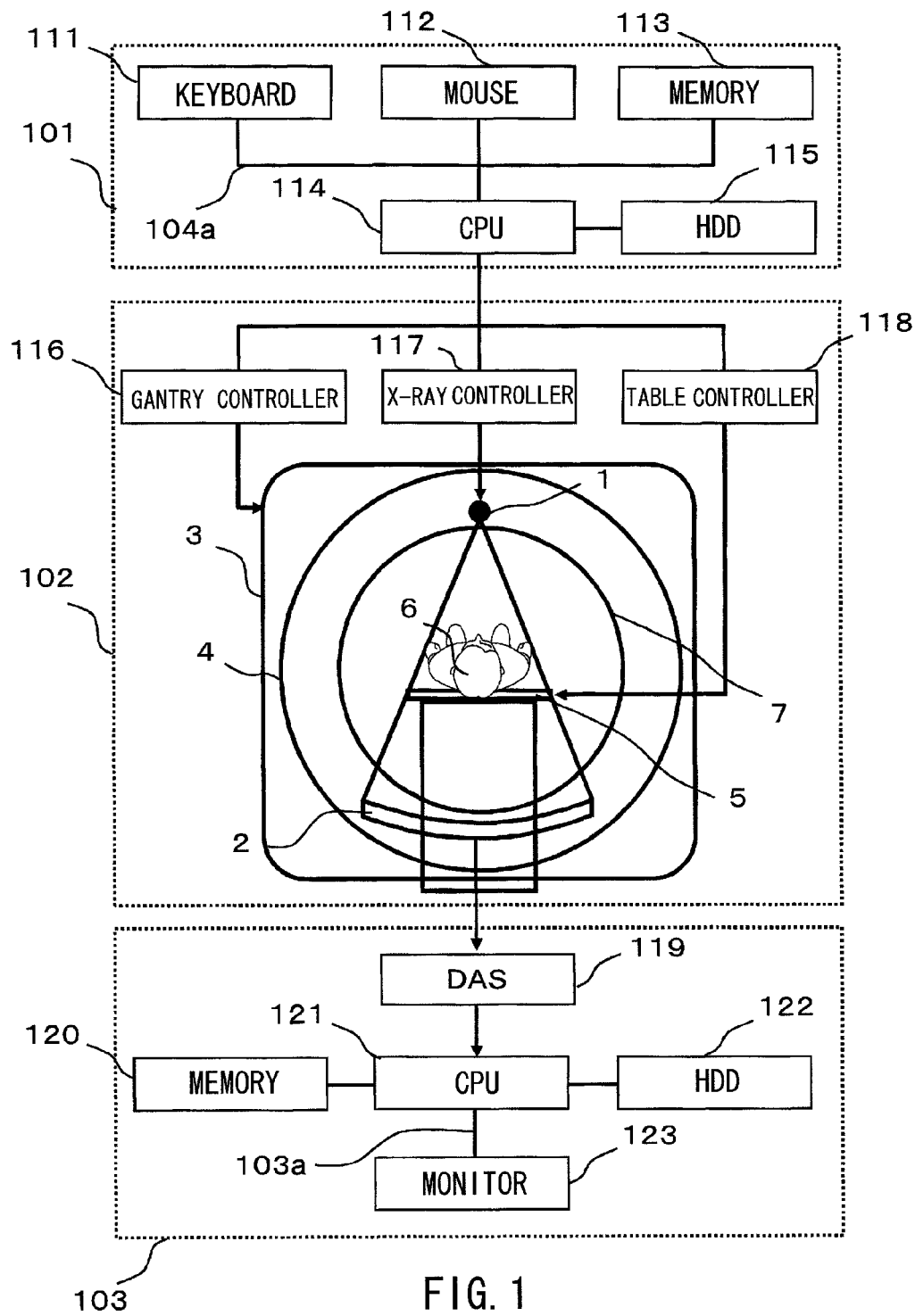
FIG. 1 is a block diagram for explaining a hardware configuration of each unit of the apparatus in the first embodiment of the proposed method.

With reference to FIG. 1, an explanation will be made as to the hardware configuration of the X-ray CT apparatus on which the adaptive filter is mounted according to the first embodiment.

The apparatus as shown in FIG. 1 is provided with an input unit 101 for inputting imaging conditions such as an X-ray irradiation condition and a condition of the adaptive filter, an imaging unit 102 for controlling the imaging and performing X-ray irradiation and detection, and the image calculation unit 103 for performing correction on signals being detected and image reconstruction for outputting an image. It is to be noted that the input unit 101 and the image calculation unit 103 are not necessarily configured integrally with the apparatus. For example, the input unit and the image calculation unit placed at a remote site may be connected to the apparatus via the network, thereby performing the input processing and image calculation processing.

The input unit 101 incorporates, for instance, an input unit of imaging condition, such as a keyboard 111, a mouse 112, a pen tablet, and a touch panel, a central processing unit 114, and a storage unit such as an HDD (Hard Disk Drive) 115. Predetermined programs are expanded and started, allowing the central processing unit 114, the memory 113, and the HDD 115, to process the data inputted from the keyboard 111, the mouse 112, and the like. Accordingly, the central processing unit 114 transmits a control signal to the imaging unit 102. Connection among each of constitutional elements in the input unit 101 is established through the data bus 104a.

The imaging unit 102 incorporates an X-ray tube 1, a gantry 3, and a table 5, together with an X-ray controller 117, a gantry controller 116, and a table controller 118 for controlling operations of the respective elements. The imaging unit 102 further incorporates the X-ray tube 1 and the X-ray detector 2 for irradiation and detection of X-rays. A representative example of a distance between a point of X-ray generation of the X-ray tube 1, and an X-ray input plane of the X-ray detector 2 is 1000 [mm]. At the center of the gantry 3, there is provided a circular aperture 7 for placing the subject 6 and the table 5. A representative example of the diameter of the aperture 7 is 700 [mm]. A representative example of the time required for a rotation of a rotating plate 4 is 1.0 [s]. A publicly known X-ray detector made up of a scintillator, a photo diode, and the like, is used as the X-ray detector 2. The X-ray detector 2 includes a large number of detection elements, not illustrated, which are arranged in a circular arc shape, at an equal distance from the X-ray tube 1, and a representative example of the element number (hereinafter, referred to as "channel number") is 950. A representative example of the size of each detection element in the channel direction is 1 [mm]. The number of imaging times per rotation of the imaging unit 102 is 900, and one imaging is performed every time when the rotating plate 4 rotates by 0.4 degrees. It is to be noted that specifications described above are not limited to those respective values, but they may be changed variously in accordance with the configuration of the X-ray CT apparatus.

The image calculation unit 103 incorporates a data acquisition system (DAS) 119, a memory 120, a central processing unit 121, an HDD 122, and a monitor 123. The DAS 119 converts the signals detected by the X-ray detector 2 of the imaging unit 102 into digital signals. The central processing unit 121 and the memory 120 expand and start predetermined programs, thereby performing correction of the digital signals and image reconstruction. In addition, the HDD 122 and the like perform storing data and inputting/outputting data. The CT image being reconstructed is displayed on the monitor 123 such as a liquid crystal display and a CRT. Connection among each of constitutional elements of the image calculation unit 103 is established via the data bus 103a.

Figure 2:
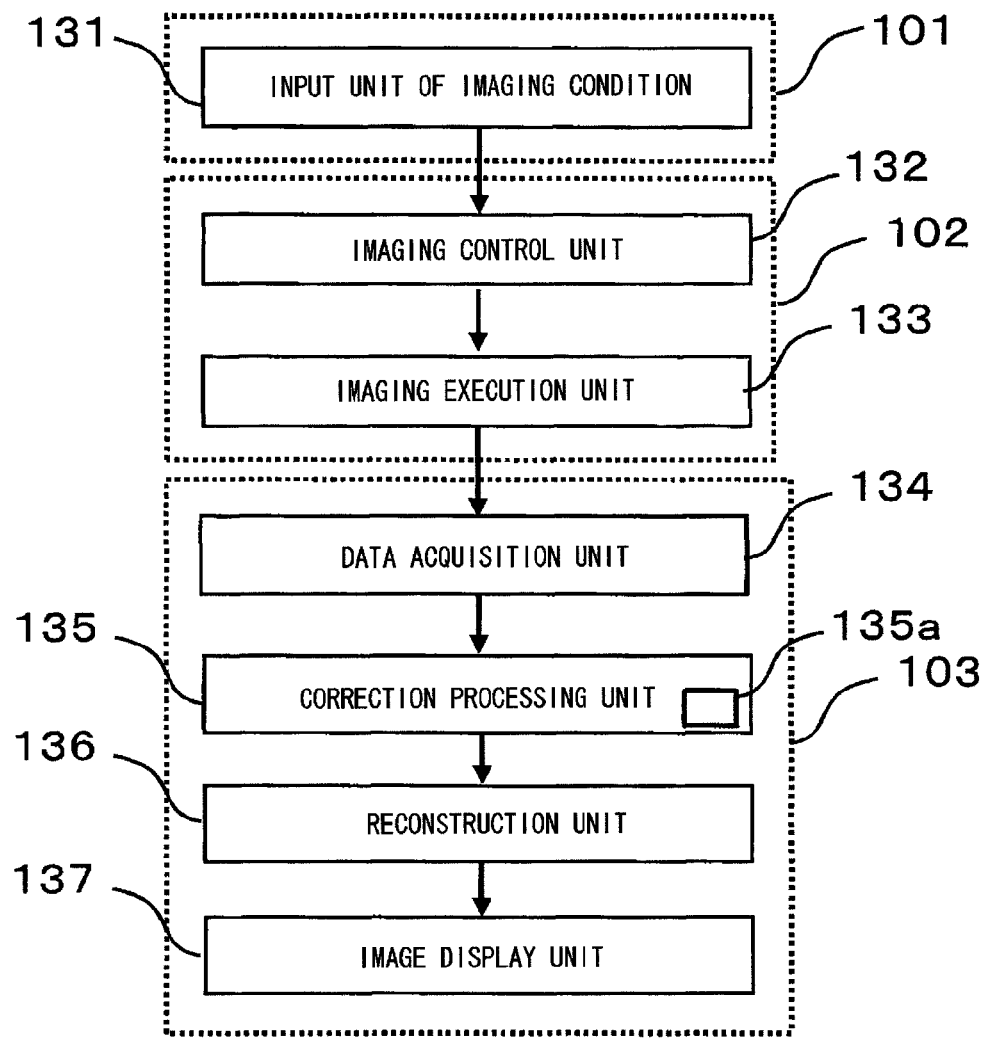
FIG. 2 is a block diagram showing functions of each unit and a flow of operation in the first embodiment.

Next, with reference to FIG. 2, functions at the time of imaging will be explained as to the X-ray CT apparatus on which the adaptive filter is mounted according to the first embodiment. As shown in FIG. 2, the input unit 101 of the X-ray CT apparatus illustrated in FIG. 1 functions as the input unit of imaging condition 131 through which imaging conditions are inputted. The imaging unit 102 functions as an imaging control unit 132 for controlling imaging based on the imaging conditions inputted through the input unit of imaging condition 131, and an imaging execution unit 133 for performing irradiation and detection of X-rays. The image calculation unit 103 functions as a data acquisition unit 134 for converting a signal being detected to a digital signal, a correction processing unit 135 for making a correction on the digital signal, a reconstruction unit 136 for performing image reconstruction on projection data being corrected, and an image display unit 137 for outputting a CT image being reconstructed. The adaptive filter unit 135a for performing adaptive filter processing is placed in the correction processing unit 135.

With reference to FIG. 2, a flow of operation of each unit at the time of imaging will be further explained. The input unit of imaging condition 131 allows the monitor 123 to display a monitor screen 141 for accepting an input of the imaging conditions as shown in FIG. 3 via the central processing unit, and the like. An operator uses a mouse 112, a keyboard 111, and the like, to set the imaging conditions, such as an imaged region, X-ray tube voltage, quantity of X-ray tube current. Specifically, the monitor screen 141 for setting imaging condition includes a select list of imaged region 142 for selecting an imaged region, a setting unit of X-ray condition 143 for setting the X-ray tube voltage and the quantity of X-ray tube current which correspond to irradiated X-ray energy and an output amount thereof, a select list of adaptive filter processing 144, a select list of a direction of adaptive filter processing 145, and a selecting unit of adaptive filter mode 146 for deciding a degree of smoothing by the filter.

The operator selects an imaged region from the select list of imaged region 142. By way of example, thorax, abdomen, head, neck, spine, hip joint, extremity, or the like, can be selected as a region. It is further possible to configure that tissues such as the heart, fat, and vessel are selectable, in addition to the regions above. The operator designates the X-ray tube voltage and the quantity of X-ray tube current in the setting unit of X-ray condition 143. A representative example of the X-ray tube voltage value is 120 [kV], and a representative example of the quantity of X-ray tube current is 200 [mA·s]. In the present embodiment, X-ray having one type of energy spectrum is assumed. As for a multi-energy CT using two or more types of X-rays, it is possible to configure similar settings by providing additional items to set the X-ray tube voltage and the quantity of X-ray tube current.

When it is selected to perform the adaptive filter processing (in FIG. 3, "Yes" is selected), the operator is allowed to select a direction for the processing, from three dimensions; a channel direction, a direction of projection angle, and a slice direction. The direction for the adaptive filter processing is not limited only to one direction, and it is possible to select two or more directions, as shown in FIG. 3, such as both the channel direction and the direction of projection angle. As for the direction of processing, three dimensions (three directions) shown in FIG. 3 are just one example, and it is further possible to apply the filter to the direction of imaging time, for the data items different in imaging time such as imaging the heart.

With regard to the selecting unit of adaptive filter mode 146, the operator selects one mode from a low dose mode, a high quality mode, and a manual setting mode. For example, in the low dose mode, FWHM (full width at half maximum) d of filter function which relates to a degree of smoothing (see FIG. 9(b) described below) is set to be a predetermined wide range value for the imaged region selected from the select list of imaged region 142, thereby intensifying an effect of smoothing. Accordingly, it is possible to reduce artifacts which tend to occur in low dose situations. In the high quality mode, the artifacts are less prone to occur relative to the low dose situations, and therefore, FWHM d of filter function is set to be a predetermined narrow range value, thereby turning down an effect of smoothing. By setting the mode of the adaptive filter as described above, it is possible to adjust the degree of smoothing in accordance with the imaging condition. Therefore, the artifacts can be reduced while suppressing deterioration of spatial resolution due to the smoothing.

In the selecting unit of adaptive filter mode 146 of the monitor screen 141, an entry field 146a for inputting a numeric value of FWHM d of filter function is provided, enabling the operator to input a numeric value. By way of example, "corresponding to 5 data items" as FWHM as shown in FIG. 3 indicates that when smoothing is performed on the data item of one channel, the smoothing is performed on the data item of the pertinent channel together with the data items of four channels which are adjacent to the above one channel.

The input unit of imaging condition 131 is not limited to the configuration which accepts the settings on the monitor screen 141 for setting the imaged region, the X-ray condition, and the adaptive filter, and it is further possible to accept an input of the imaging condition according to another method. It is further possible to store the imaging condition in the HDD 115 in advance, and on this occasion, it is not necessary for the operator to input the imaging condition each time.

The operator designates a position to be imaged of the subject 6, by using the mouse 112, the keyboard 111, and the like, and thereafter gives a directive to start imaging. When the start of imaging is directed, the imaging control unit 132 allows the table controller 118 to move the table 5. Accordingly, the subject 6 is moved in an approximately vertical direction with respect to the rotating plate 4, and the movement is stopped to place the subject 6 at the point where the position of the subject 6 to be imaged matches the position that is designated by the operator. On the other hand, the gantry controller 116 of the imaging control unit 132 starts rotation of the rotating plate 4 via a drive motor simultaneously with the directive for starting the imaging. At the time when rotation of the rotating plate 4 comes to a constant speed and placing of the subject 6 is completed, the X-ray controller 117 controls X-ray irradiation timing from the X-ray tube 1 of the imaging execution unit 133 and imaging timing of the X-ray detector 2 of the imaging unit.

In the present embodiment, imaging is performed while the rotating plate 4 is rotating, and an energy spectrum and an output amount of X-rays being irradiated are determined according to the X-ray tube voltage and the quantity of X-ray tube current of the X-ray tube 1, being set previously.

In the present embodiment, the X-rays having one type of energy spectrum are used. However, it is also possible to perform a multi-energy CT imaging which switches the X-ray tube voltage per rotation at a high speed to irradiate X-rays having two or more types of energy spectra to acquire imaged data.

Next, the imaging execution unit 133 allows the X-ray detector 2 to detect an X-ray photon which has passed through the subject 6. The data acquisition unit 134 of the image calculation unit 103 converts X-ray detecting data from the X-ray detector 2 to a digital signal according to the DAS 119. The X-ray detecting data acquired by the data acquisition unit 134 is stored in the memory 120. The correction processing unit 135 makes a correction on this data, such as an offset correction for calibrating the X-ray signal to zero, and a publicly known air calibration processing for correcting sensitivity between detectors, and acquires projection data of the subject 6. On this occasion, the adaptive filter unit 135a smoothes the X-ray detecting data and/or the projection data, thereby reducing noise that causes artifacts. Processing of the adaptive filter unit 135a of the proposed method will be explained in detail in the following description.

The reconstruction unit 136 of the image calculation unit 103 applies an arithmetic processing, using a publicly known CT image reconstruction algorithm, to the projection data value $I_{lo}$ (i, j, k) corrected by the correction processing unit 135, and accordingly, acquires a CT image representing an X-ray attenuation coefficient of the subject.

The image display unit 137 displays the CT image being calculated on the monitor 123, thereby providing information to the operator. It is to be noted that a network adapter may be used to establish connection between an external terminal and the CT apparatus, via a network such as a local area network, a telephone line, the Internet, enabling transmit-receive of the CT image between the CT apparatus and the terminal.

Next, with reference to FIG. 4 to FIG. 7, an explanation will be made as to the configuration and operation of the adaptive filter unit 135a.

Figure 4:
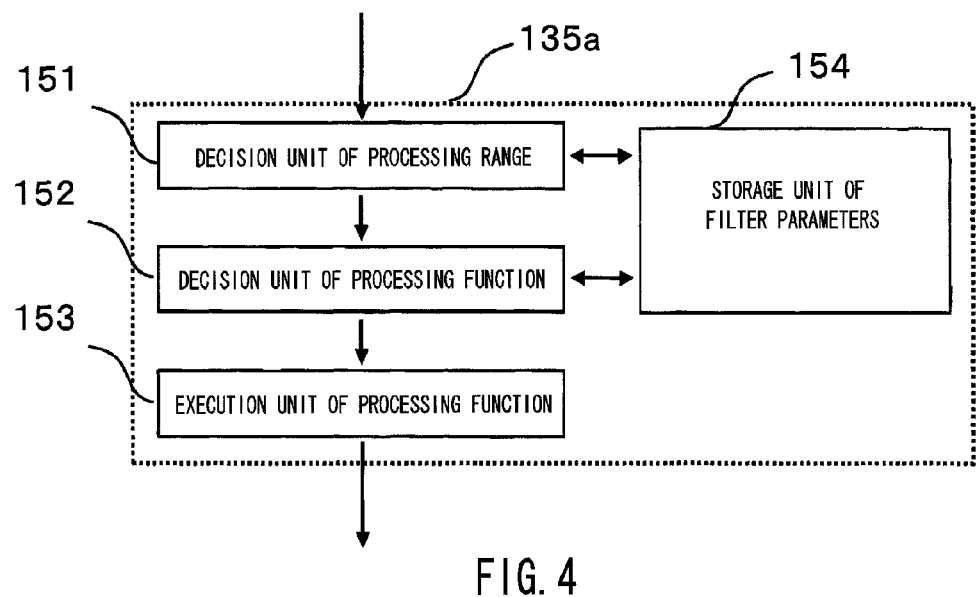
FIG. 4 is a block diagram showing a configuration of an adaptive filter unit 135a in the first embodiment.

As shown in FIG. 4, the adaptive filter unit 135a includes a decision unit of processing range 151 for setting an application range of the adaptive filter to the X-ray detecting data acquired by the data acquisition unit 134, a decision unit of processing function 152 for calculating a filter function from the processing range being set, an execution unit of processing function 153 for executing smoothing by using the filter function being calculated, and a storage unit of filter parameters 154 from which a parameter required for the adaptive filter is read in accordance with the X-ray irradiation condition, the filter condition, and the like, which are inputted by the input unit of imaging condition 131.

Figure 5:
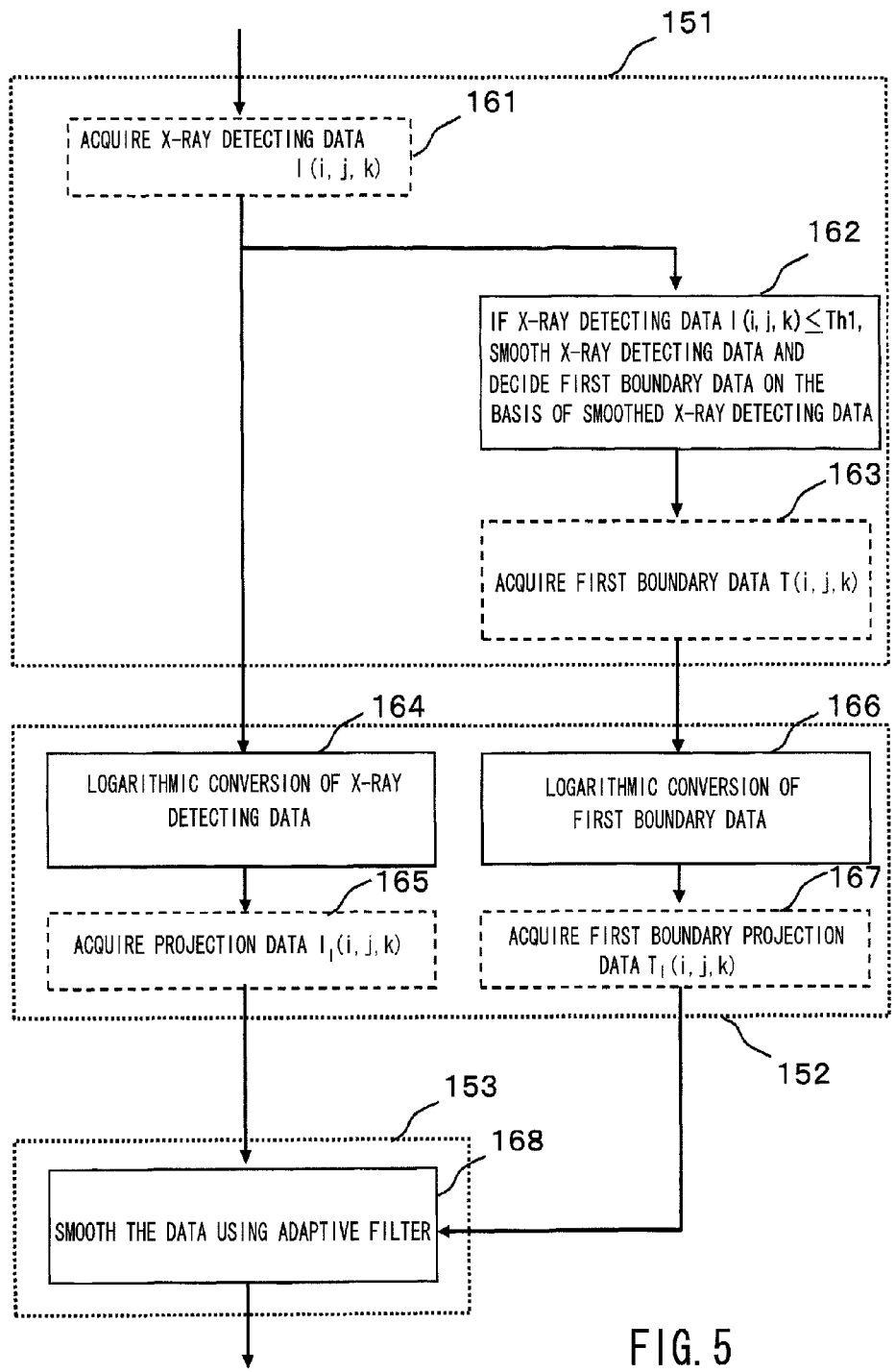
FIG. 5 is a flowchart showing a flow of the processing of the adaptive filter unit 135a in the first embodiment.
Figure 6:
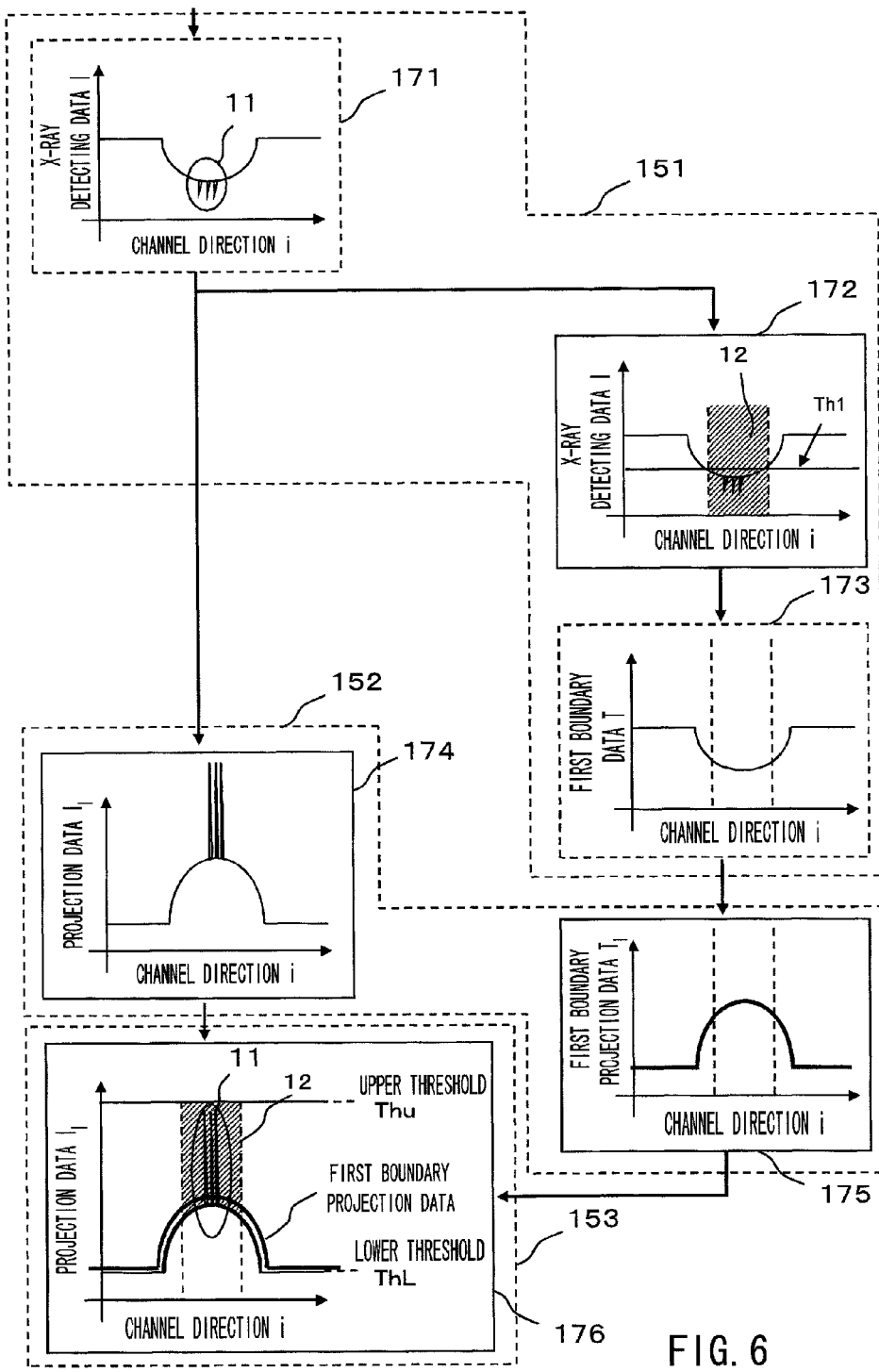
FIG. 6 illustrates a flow of processing of the adaptive filter unit 135a and the data obtained at each process in the first embodiment.

With reference to FIG. 5, the operation of the adaptive filter unit 135a will be explained. FIG. 6 illustrates a state of data at each point in the flow of FIG. 5.

In the step 161 of FIG. 5, the decision unit of processing range 151 acquires X-ray detecting data I (i, j, k) from the data acquisition unit 134 (see FIG. 2). This X-ray detecting data I is a data item obtained by irradiating X-ray $I_o$ and detecting an X-ray photon that has passed through the subject, and it is expressed by the following formula (1):

$$I = I_0 \exp(-\mu \cdot l) \qquad \text{Formula 1}$$

In the formula (1), the X-ray detecting data I represents an X-ray photon count [photon] after passing through the subject, $I_o$ represents an X-ray photon count [photon] without going through the subject, $\mu$ represents a linear attenuation coefficient [cm$^{-1}$], l represents a path length of transmission [cm].

Figure 7:
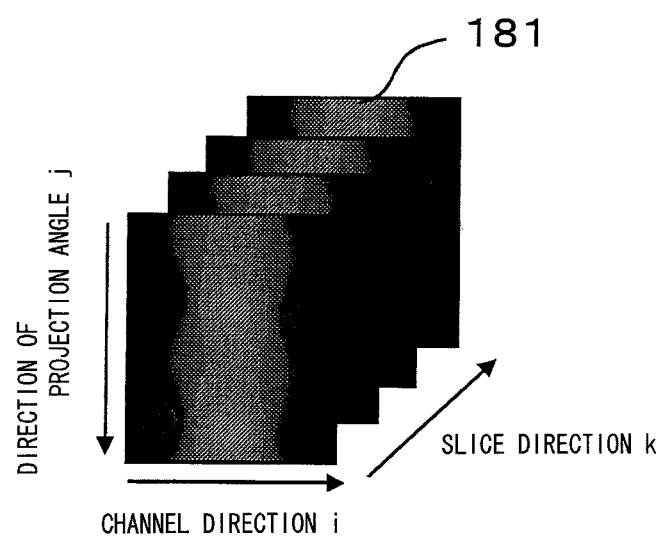
FIG. 7 illustrates X-ray detecting data acquired from the X-ray CT apparatus in the first embodiment.

The projection data 181 as shown in FIG. 7 is obtained from the X-ray detecting data I, as a result of applying a publicly known air calibration processing to the X-ray detecting data I, followed by logarithmic conversion. In this result, a gray scale is employed, showing that the higher is the attenuation coefficient of X-rays passing through the subject 6, the color becomes whiter. On the other hand, if the attenuation coefficient becomes lower, the color becomes darker. As shown in FIG. 7, the X-ray detecting data I or the projection data is made up of three directions; a channel direction i in which the X-ray detectors 2 are aligned in parallel with the tomographic direction of the subject 6, a direction of projection angle j at which the X-ray tube 1 rotates at the time of X-ray irradiation, and a slice direction k in which the X-ray detectors 2 are aligned perpendicular to the tomographic direction of the subject 6.

For example, in the case where a cylindrical-shaped homogeneous subject 6 is placed at the center of the imaging area and imaged, the X-ray detecting data I acquired in the step 161 of FIG. 5 looks like the data 171 as shown in FIG. 6, when a graph is generated assuming the channel i as the horizontal axis and values of the X-ray detecting data as the vertical axis. It is to be noted here that the projection angle j' and the slice k' are assumed as arbitrary values. In the data 171, the path l for passing through the cylindrical-shaped subject 6 is long at the center of the channel i, and therefore, the transmitting X-ray photon count is decreased, and the noise component 11 with respect to the signal is increased as indicated by the data 171 in FIG. 6. Therefore, more variations in data are found than the adjacent channel.

In the step 162, the decision unit of processing range 151 obtains a channel range (filter application range) 12 where the X-ray detecting data I is equal to or less than a predetermined threshold Th1 as indicated by the data 172 of FIG. 6, and performs smoothing processing on the X-ray detecting data I in this filter application range 12. Accordingly, the first boundary data T (i, j, k) 173 is acquired (step 163). As shown in FIG. 6, in the first boundary data T (i, j, k) 173 being obtained, the noise component 11 has been reduced by the smoothing. This first boundary data 173 is used as a threshold ThL in the smoothing processing which uses the adaptive filter described below (step 168). It is to be noted that for easily understanding the data 173 in FIG. 6, the first boundary data T is shown also for the channel outside the filter application range 12, but as a practical matter, only the first boundary data T is calculated only in the filter application range 12.

A publicly known method can be employed for the smoothing processing in the step 162. For example, there is a method for performing convolution with the filter function (FIG. 9(b)) on the X-ray detecting data I. The smoothing processing according to the convolution will be described later.

In the step 162, two processes are performed with the use of the threshold Th1; setting of the filter application range 12, and generating the first boundary data 173. Since the filter application range 12 is an area where the X-ray detecting data I is equal to or less than the threshold Th1 and the X-ray dose is low after passing through the subject, it is configured as an area for applying the smoothing by the adaptive filter in the step 168 described below. On the other hand, in the area where the X-ray detecting data I is larger than the threshold Th1 (an area outside the range 12), the X-ray dose is high, it is configured as an area to which the smoothing is not applied. In addition, setting of the filter application range 12 may reduce a calculation amount and a memory amount in the step 163 and steps subsequent thereto as shown in FIG. 5.

The threshold Th1 can be determined according to a calculation by using a predefined arithmetic expression. It is further possible to use a constant that is obtained in advance based on experiences and experiments according to the imaging condition. When the threshold Th1 is defined by calculation, it can be decided according to the formula (2), based on the relationship of B=$\mu \cdot l$, which is a product between the attenuation coefficient and the path length of transmission, relative to the rate of X-ray photon count A=I/$I_o$.

$$\frac{dB}{dA} \leq C \qquad \text{Formula 2}$$

Figure 8:
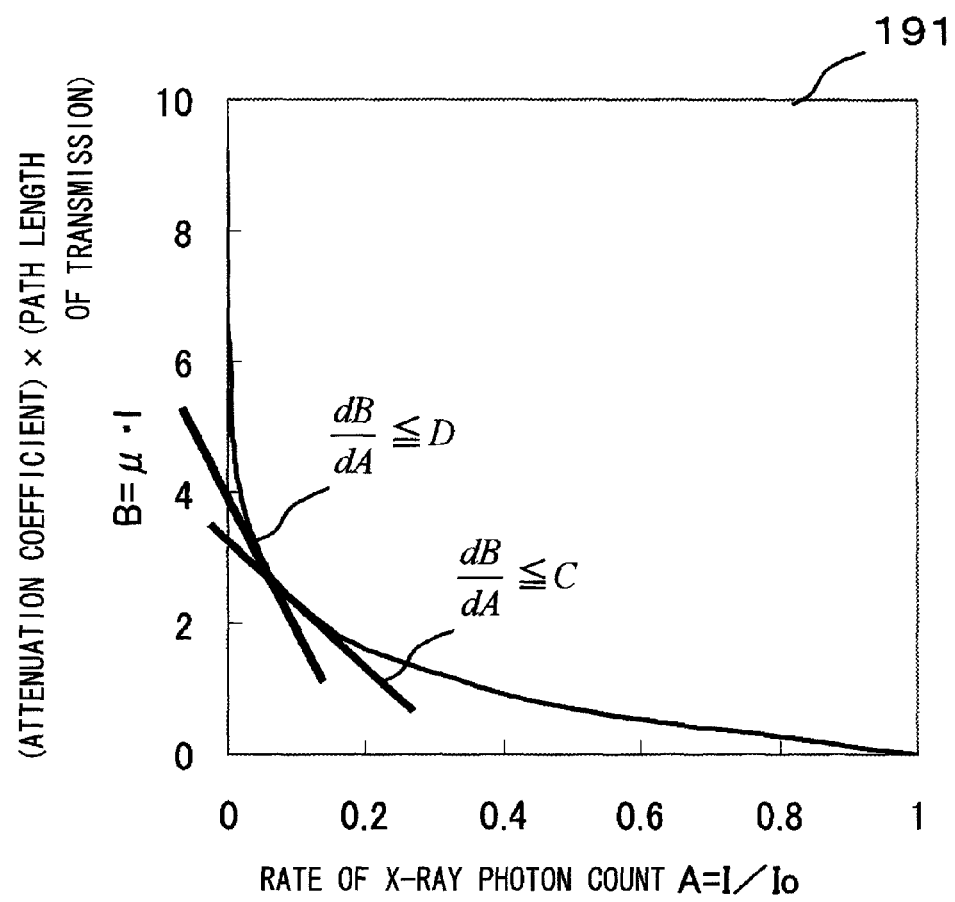
FIG. 8 is a graph for explaining a relationship between a rate of X-ray photon count and a product of attenuation coefficient and path length of transmission, in the first embodiment.

As shown in FIG. 8, the left-hand side of the formula (2) expresses variation of B with respect to small variation of A. This corresponds to the variation dB of the attenuation coefficient with respect to a component of dA that fluctuates due to noise influence. In the present embodiment, when the variation of B with respect to the small variation of A on the left-hand side is equal to or less than the constant C being predefined, the area is low in X-ray dose after passing through the subject, and therefore, it is determined that the attenuation coefficient changes drastically by a small noise fluctuation with respect to the X-ray detecting signal. Since when the condition is equal to or less than C, it is necessary to smooth the attenuation coefficient which changes significantly, Th1 is determined according to C. On this occasion, C is determined according to the X-ray irradiation condition such as the imaged region set in FIG. 3, and the filter condition such as a mode of the adaptive filter. By way of example, the relationship between the rate of X-ray photon count A and the product B of the X-ray attenuation coefficient and the path length of transmission is expressed by the formula (3). Variation of B relative to the small variation of A is expressed by the formula (4) according to the formula (2) and the formula (3).

$$B = -\log A \qquad \text{Formula 3}$$

$$\frac{dB}{dA} = -\frac{1}{A} \qquad \text{Formula 4}$$

By way of example, it is assumed that $A=I/I_o$, $B=\mu \cdot l$, $C=-100$, $I_o=10000$. The formula (2) and the formula (4) leads to $I \leq 100$, and therefore, the threshold Th1 of the step 162 is determined as 100 [photon].

When the constant is used, which is predefined as the threshold Th1, arbitrary X-ray photon count I obtained in advance by experiences and experiments according to the imaging condition can be set as the threshold. By way of example, it is possible to assume that the threshold Th1 is 200 [photon].

Next, the decision unit of processing function 152 performs a publicly known air calibration on the X-ray detecting data I (data 171 in FIG. 6) in the step 164, thereafter performs the logarithmic conversion, and acquires the projection data value $I_l$ (i, j, k) (data 174 in FIG. 6) of the attenuation coefficient as expressed by the formula (5) (step 165).

$$\mu \cdot l = -\log\left(\frac{I}{I_0}\right) = I_l \qquad \text{Formula 5}$$

The decision unit of processing function 152 performs the logarithmic conversion also on the first boundary data T (data 173 of FIG. 6) in the step 166. According to this conversion, the first boundary projection data $T_l$ (i, j, k) (data 175 in FIG. 6) is acquired (step 167).

Next, the execution unit of processing function 153 performs the smoothing processing by using the adaptive filter in the step 168. In the present embodiment, as expressed by the formula (6), the projection data $I_l$ (i, j, k) is added to the projection data $I_{lw}$ (i, j, k) that is obtained by performing the smoothing processing on the projection data $I_l$ (i, j, k) according to a publicly known method, with weight δ being assigned thereto, whereby the projection data $I_{lo}$ (i, j, k) after the adaptive filter is applied is obtained. On this occasion in the present embodiment, as expressed by the formulas (7) to (9), by using a lower threshold ThL (i, j, k) and an upper threshold Thu (i, j, k), conditions are analyzed according to a value of the projection data $I_l$, and different weight δ is assigned to each condition. The lower threshold ThL (i, j, k) and the upper threshold Thu (i, j, k) are determined based on the first boundary projection data $T_l$ (i, j, k). Specifically, the first boundary projection data $T_l$ (i, j, k) is used as the ThL (i, j, k). As the threshold Thu, a predetermined value decided according to ThL is used, for example, Thu=K·ThL (K is a positive real number). In the case where the threshold Thu is defined by calculation, it is determined according to the formula (10), based on the relationship $B=\mu \cdot l$, which is a product of the X-ray attenuation coefficient and the path length of transmission, relative to the rate of X-ray photon count $A=I/I_o$. As shown in FIG. 8, the formula (10) expresses that when a variation of B with respect to a small variation A on the left-hand side is equal to or less than the constant D, an area is extremely low in X-ray dose after passing through the subject. Therefore, it is determined that just a small noise fluctuation may drastically change the attenuation coefficient with respect to an X-ray detecting signal. Consequently, under the condition equal to or less than D, it is necessary to smooth the attenuation coefficient which changes drastically, and Thu is determined according to D. On this occasion, D is decided according to the X-ray irradiation condition such as an imaged region and the filter condition such as the adaptive filter mode, which are set in FIG. 3. In the present embodiment, by way of example, it is defined that D=−200 and the threshold Thu of the data 176 is decided as 2.0.

When a predefined constant is used as the threshold Thu, it is possible to set an arbitrary X-ray photon count I as the threshold, which is obtained in advance by experiences and experiments according to the imaging condition. The threshold Thu may be set to 1.5, for instance.

$$I_{lo}[i] = \delta \cdot [i] + (1 - \delta) \cdot I_l[i] \qquad \text{Formula 6}$$

$$\delta = \frac{(\text{Formula 10} - ThL)}{Thu - ThL} \quad ThL \leq I_l[i] \leq Thu \qquad \text{Formula 7}$$

$$\delta = 0 \quad I_l[i] < ThL \qquad \text{Formula 8}$$

$$\delta = 1 \quad I_l[i] > Thu \qquad \text{Formula 9}$$

$$\frac{dB}{dA} \leq D \qquad \text{Formula 10}$$

In other words, when the projection data $I_l$ is less than the lower threshold ThL (=first boundary projection data $T_l$), it is assumed δ=0 as expressed by the formula (8), thereby setting the projection data $I_l$ (i, j, k), as it is, as the projection data $I_{lo}$ (i, j, k) after the application of the adaptive filter.

When the projection data $I_l$ more than the upper threshold Thu, it is assumed δ=1 as expressed by the formula (9), thereby setting the data $I_{lw}$ (i, j, k) after the smoothing processing as the projection data $I_{lo}$ (i, j, k).

When the projection data $I_l$ is equal to or more than the lower threshold ThL (=the first boundary projection data $T_l$) and equal to or less than the upper threshold Thu, the formula (7) is used to calculate a value, by dividing a difference between the projection data $I_l$ and ThL by a difference between ThL and Thu, thereby using the calculated value as the weight δ. The weight δ being obtained is used in the calculation of the formula (6), and as to the projection data $I_l$ which exceeds the lower threshold ThL (=the first boundary projection data $T_l$), if the ratio of the excess amount from the lower threshold ThL is larger, the more data $I_{lw}$ after the smoothing processing is added to the projection data $I_l$. Consequently, as the ratio of the excess from the lower threshold ThL (=the first boundary projection data $T_l$) becomes larger, it is possible to obtain the smoothed data $I_{lw}$ (i, j, k) more intensively.

As thus described, in the present embodiment, the smoothing processing is performed on the X-ray detecting data value I obtained from the subject, and thereafter, the logarithmic conversion is applied thereto to obtain the first boundary projection data $T_l$ (i, j, k). By using this obtained first boundary projection data, conditions of the projection data $I_l$ of the subject are analyzed, thereby deciding the intensity (degree) of the smoothing which is applied to the projection data $I_l$ (i, j, k) depending on the conditions. Consequently, it is possible to apply the smoothing processing with a degree appropriate for each subject, and compared to the case where the same filter condition is used for the projection data in all the channels irrespective of the subject, artifacts can be removed, while suppressing deterioration of the spatial resolution. With the configuration above, even when the imaging is performed with a low dose, the artifacts can be reduced, and therefore low-dose imaging becomes implementable.

In the present embodiment, since the filter application range 12 is set and the first boundary projection data $T_l(i, j, k)$ is generated, it is not necessary to perform the smoothing processing to all the channels, and therefore the arithmetic processing amount can be reduced.

An explanation will be made as to an arithmetic operation method of the smoothed data $I_{lw}(i, j, k)$ that is used in the above formula (6). The smoothed data $I_{lw}(i, j, k)$ is the data obtained by applying a publicly known smoothing processing on the projection data $I_l(i, j, k)$. By way of example, convolution is used as described below.

As illustrated by the data 176 shown in FIG. 6, the convolution is performed on the projection data $I_l(i, j, k)$ that is included in the filter application range 12. Specifically, as expressed by the formula (11), the smoothed data $I_{lw}(i, j, k)$ is obtained by the convolution with the filter function W (i, j, k) 202 as shown in FIG. 9(b), on the projection data $I_l$ 201 of the channel i at arbitrary angle j' and slice k' as shown in FIG. 9(a).

$$I_{lw}[i] = \sum_{a=i-\frac{d}{2}}^{i+\frac{d}{2}} w[a] \cdot I_l[a]$$ Formula 11

Figure 9:
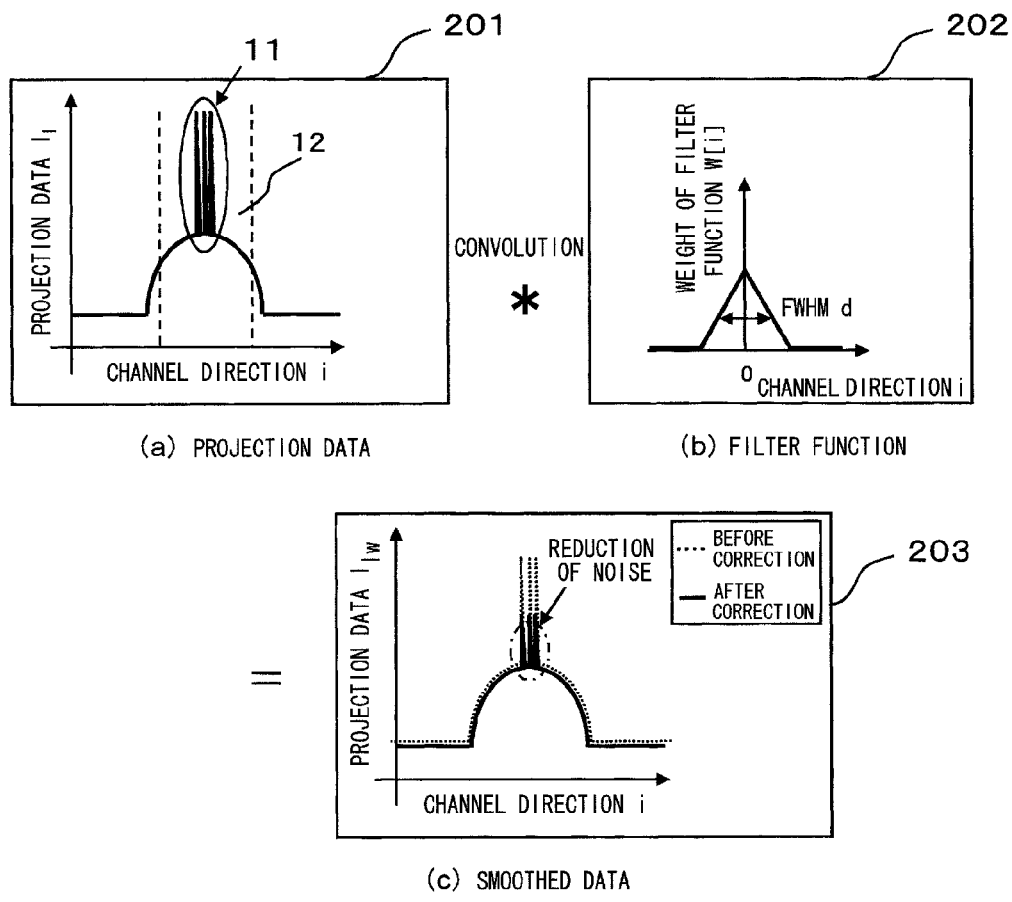
FIG. 9 illustrates the convolution by the adaptive filter unit 135a in the first embodiment.

The filter function W (i, j, k) 202 is represented by the channel direction i being the horizontal axis, the weight W[i] being the vertical axis, and FWHM d as shown in FIG. 9(b). A value of FWHM d that is set in the entry field 146a in the monitor screen 141 as shown in FIG. 3 is used as the FWHM d. The area of the filter function is standardized to 1. It is to be noted that the filter function 202 is not limited to the function which forms a triangle as illustrated in FIG. 9(b). For example, it is also possible to use other processing, such as moving average processing in which the weight in each channel is assumed as constant, and median filter processing.

It is found that as a result of the convolution, the noise component 11 of the projection data $I_l(i,j,k)$ as shown in FIG. 9(a) is reduced as seen in the smoothed data $i_{lw}(i,j,k)$ 203 in FIG. 9(c). In the present embodiment, the smoothed data $I_{lw}(i,j,k)$ 203 being obtained is added to the projection data $I_l(i, j, k)$ in accordance with the weight δ, as expressed by the formula (6), thereby acquiring the projection data $I_{lo}(i, j, k)$ after the adaptive filter is applied.

Figure 10:
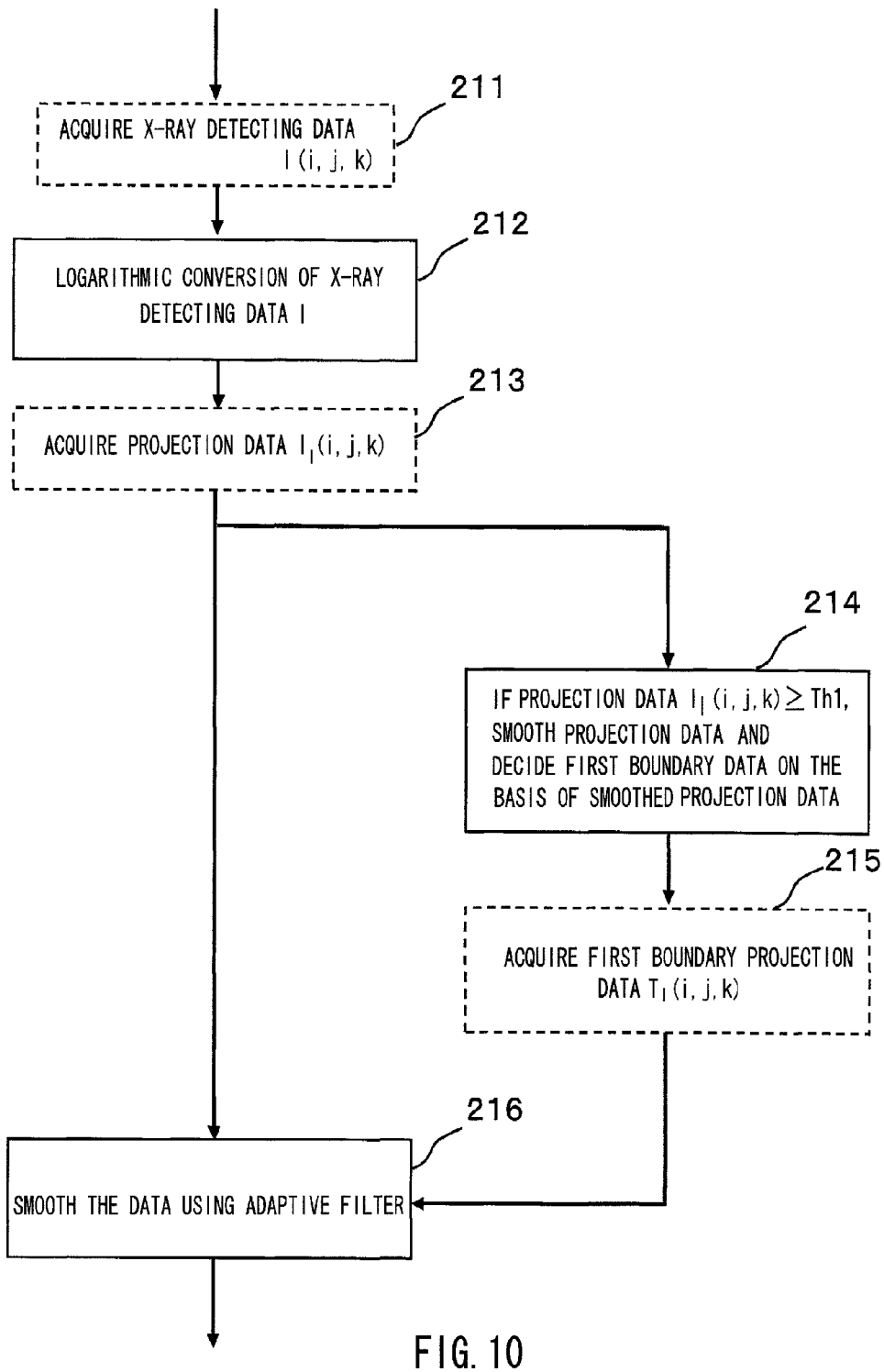
FIG. 10 is a flowchart for explaining a procedure to generate the first boundary projection data from the projection data after the logarithmic conversion, and perform the smoothing processing in the first embodiment.

In the present embodiment, a part of the X-ray detecting data I is smoothed to generate the first boundary data T and thereafter it is subjected to the logarithmic conversion to obtain the first boundary projection data $T_l$. However, the procedure is not limited to this, and it is further possible to firstly perform the logarithmic conversion on the X-ray detected data I, and subsequently the projection data $I_l$ is smoothed to generate the first boundary projection data $T_l$. With reference to FIG. 10, this processing will be explained. The X-ray detecting data I being acquired is subjected to the logarithmic conversion, so as to obtain the projection data $I_l$ (step 211, 212, and 213). Next, as to the range in which the projection data $I_l$ satisfies equal to or more than a predetermined threshold Th1 (the filter application range), the projection data $I_l$ is smoothed and the first boundary projection data $T_l$ (i, j, k) is calculated (steps 214 and 215). Accordingly, in the step 216, in the same manner as the embodiment described above, the execution unit of processing function 153 as shown in FIG. 4 performs the smoothing processing with the use of the adaptive filter according to the formulas (6) to (9). As a result, reduction of the artifacts is achieved.

Figure 11:
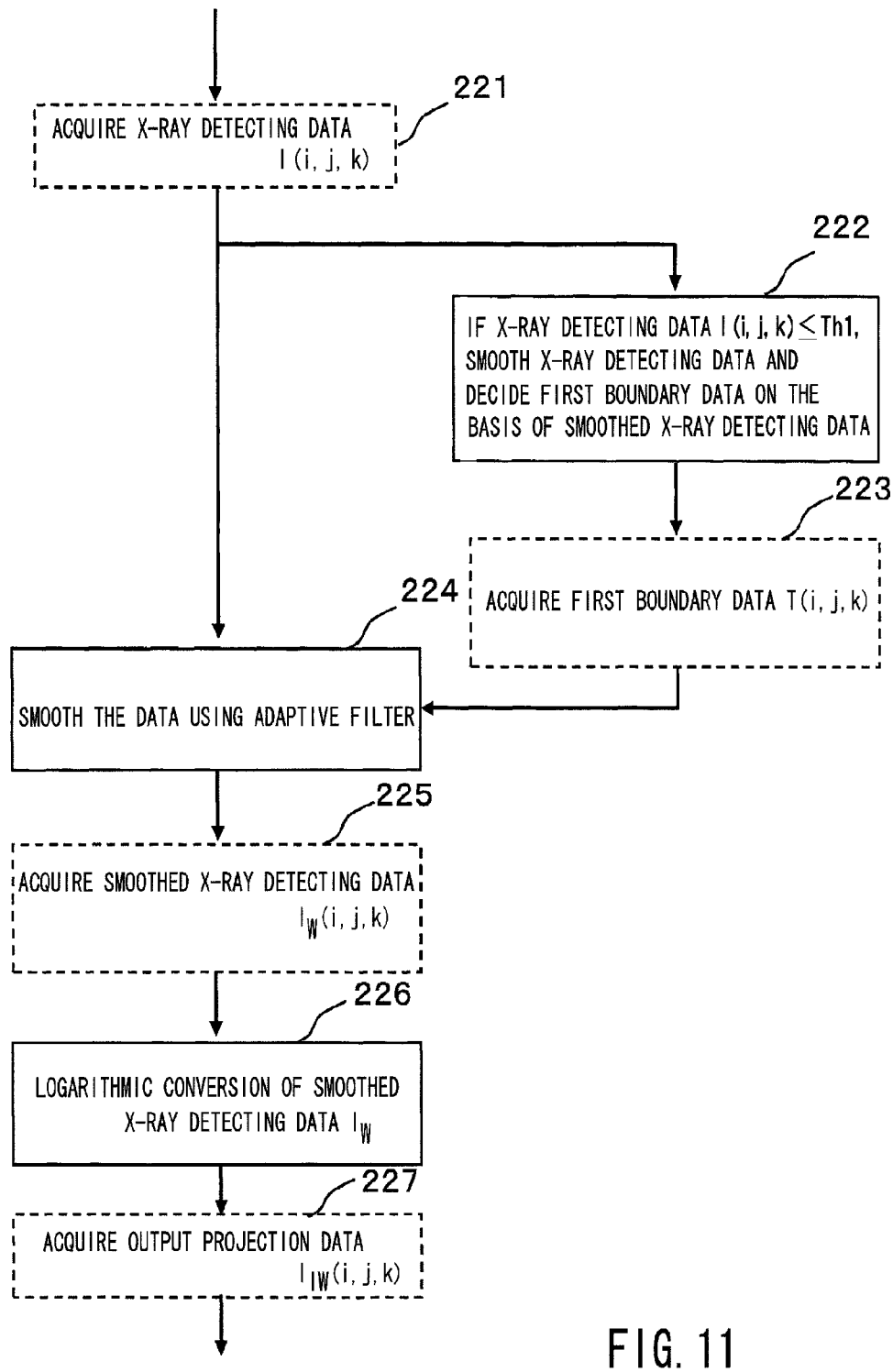
FIG. 11 is a flowchart for explaining a procedure to perform the smoothing processing on the X-ray detecting data by using the first boundary data in the first embodiment.

In the embodiment, smoothing by the adaptive filter is performed on the projection data $I_l$ by way of example. However, as shown in FIG. 11, the first boundary data T obtained by smoothing the X-ray detecting data I before the logarithmic conversion may be used as the threshold, and the first boundary data T is compared with the X-ray detecting data I to analyze conditions and set a weight δ as expressed by the formulas (7) to (9). Accordingly, it is possible to smooth the X-ray detecting data I, while appropriately switching the degree of the smoothing as expressed by the formula (6). With reference to FIG. 11, this processing will be explained. Firstly, when the acquired X-ray detecting data I satisfies equal to or less than the threshold Th1, the X-ray detecting data I is smoothed to obtain the first boundary data T (i, j, k) (steps 221, 222, and 223).

In the steps 224 and 225, the first boundary data T (i, j, k) is used as the threshold ThL, and conditions of the X-ray detecting data I is analyzed depending on its value, as expressed by the formulas (7) to (9), thereby setting the weight δ. With the use of the weight δ, the X-ray detecting data I is smoothed while appropriately switching the degree (weight) of smoothing according to the formula (6), and smoothed X-ray detecting data $I_W(i, j, k)$ can be acquired. For the smoothing, for instance, there is a method of convolution with the filter function on the X-ray detecting data I. Next, in the steps 226 and 227, the smoothed X-ray detecting data $I_W$ is subjected to the logarithmic conversion, whereby the smoothed projection data $I_{lW}$ (i, j, k) is acquired. Consequently, it is possible to acquire the smoothed projection data $I_{lw}$ (I, j, k) which has been smoothed while appropriately switching the degree of smoothing depending on the subject in the same manner as the embodiment described above. Also in the processing as shown in FIG. 11, the application range of the smoothing processing is limited according to the threshold Th1 for the X-ray detecting data before the logarithmic conversion, and therefore, the calculation amount and the memory amount can be reduced in the step 223 and the steps subsequent thereto as shown in FIG. 11.

In the embodiment as described above, the X-ray detecting data I is compared with the threshold Th1 to decide the filter application range 12. However, it may be decided from the projection data $I_l$ that is obtained by subjecting the X-ray detecting data to the logarithmic conversion. By way of example, a threshold E is decided from the attenuation coefficient of the projection data $I_l$, and the range being larger than E is set as the filter application range 12. The threshold E may be assumed as E=1.0 [cm$^{-1}$], for instance.

In the present embodiment, the filter function 202 is generated each time of imaging by using FWHM d that is inputted by the operator. However, it is also possible to prestore in the storage unit of filter parameters 154, the filter function 202 and the like for each imaging condition. Consequently, the decision unit of processing range 151, the decision unit of processing function 152, and the execution unit of processing function 153 are allowed to acquire the filter function 202 just by referring to the storage unit of filter parameters 154, and therefore, there is an advantage that a higher speed arithmetic operation can be achieved.

In the present embodiment, a biomedical X-ray CT apparatus is shown as an example. However, it goes without saying that the proposed method may be applied to an X-ray CT apparatus intended for non destructive inspections, such as an explosive inspection and a manufacture inspection. In the present embodiment, a publicly known third-generation multi-slice X-ray CT apparatus is shown as an example. However, the proposed method is applicable to a publicly known first, second, and fourth-generation X-ray CT apparatus, and it is also applicable to a publicly known single-slice X-ray CT apparatus and an electron beam CT.

Second Embodiment

In the second embodiment, a part of the X-ray detecting data is smoothed and then subjected to the logarithmic conversion to generate the first boundary projection data in the same manner as the first embodiment, and in addition, a second boundary projection data is generated by performing the logarithmic conversion on the X-ray detecting data, followed by smoothing a part thereof. One of the two types of boundary projection data is selected for each channel, and the boundary projection data being selected is used as the threshold ThL in the same manner as the first embodiment. The projection data is compared with the boundary projection data being selected (threshold ThL) and a degree of the smoothing is switched, thereby performing the smoothing operation on the projection data in accordance with the degree of the smoothing.

Accordingly, in the present embodiment, smoothing with a different threshold using the second boundary projection data can be performed at a different degree of smoothing for the area outside the range 12, the range 12 being smoothed by the first boundary projection data in the first embodiment. By way of example, as for the first boundary projection data, an area with a low X-ray dose after passing through the subject is decided as the smoothed area (filter application range 12) based on the threshold Th1 as explained in the first embodiment, but as for the second boundary projection data, an area outside the filter application range (filter application range 13), also being low in X-ray dose, is configured as the smoothed area.

By way of example, smoothing is performed by using the first boundary projection data as the threshold ThL for the area (filter application range 12) where the artifacts are supposed to be reduced on a priority basis, since the X-ray dose after passing through the subject is extremely low. On the other hand, the second boundary projection data is used as the threshold ThL for smoothing the area where the artifacts are smaller relative to the filter application range 12 and the information of the subject is required to be held on a priority basis. Consequently, it is possible to change the degree of smoothing by using a threshold which is different depending on the area of the X-ray detecting data and/or the projection data, and therefore, deterioration of spatial resolution can be suppressed while the artifacts are reduced.

Figure 12:
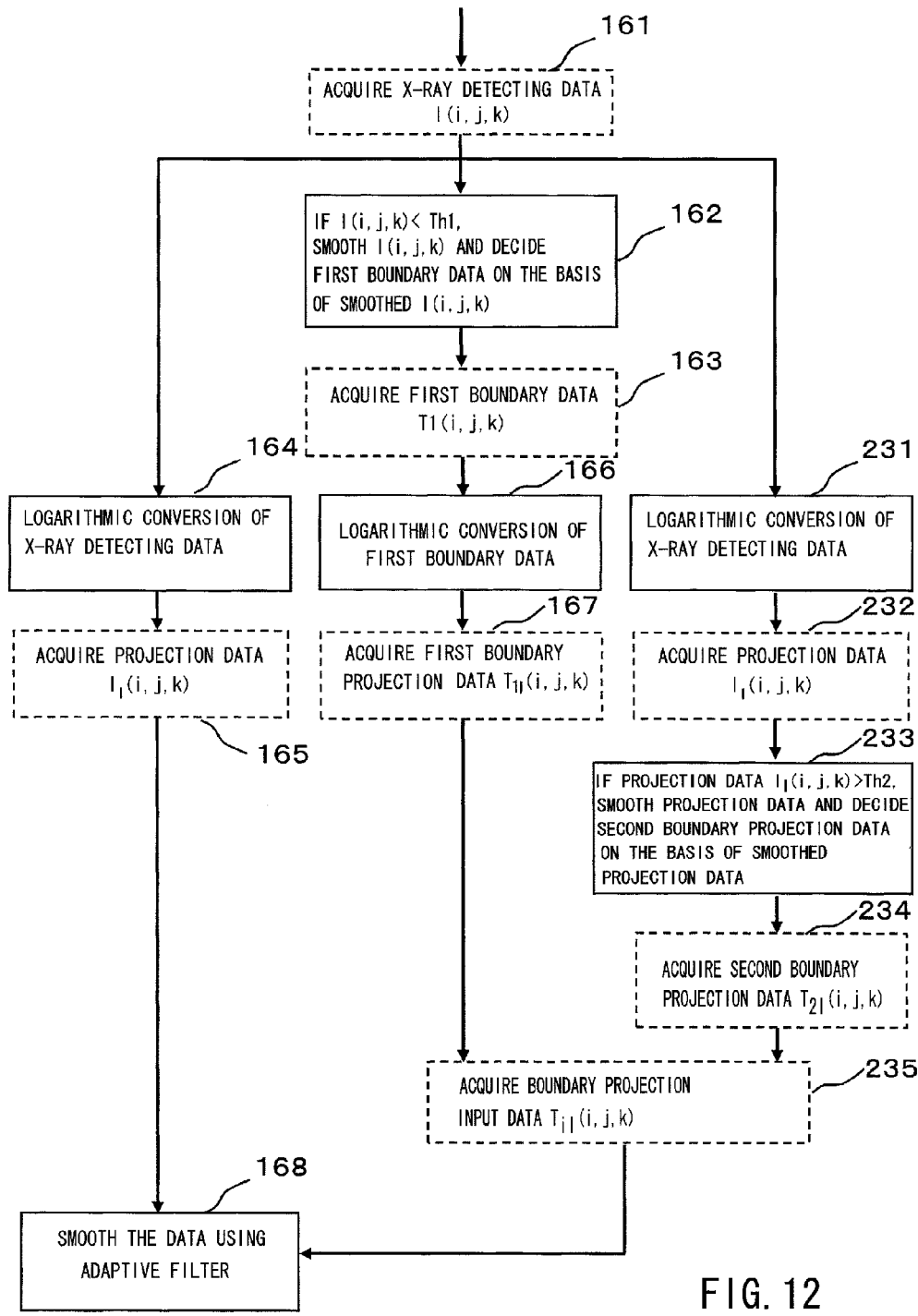
FIG. 12 is a flowchart for explaining a flow of the smoothing processing by the adaptive filter unit 135a in a second embodiment of the proposed method.
Figure 13:
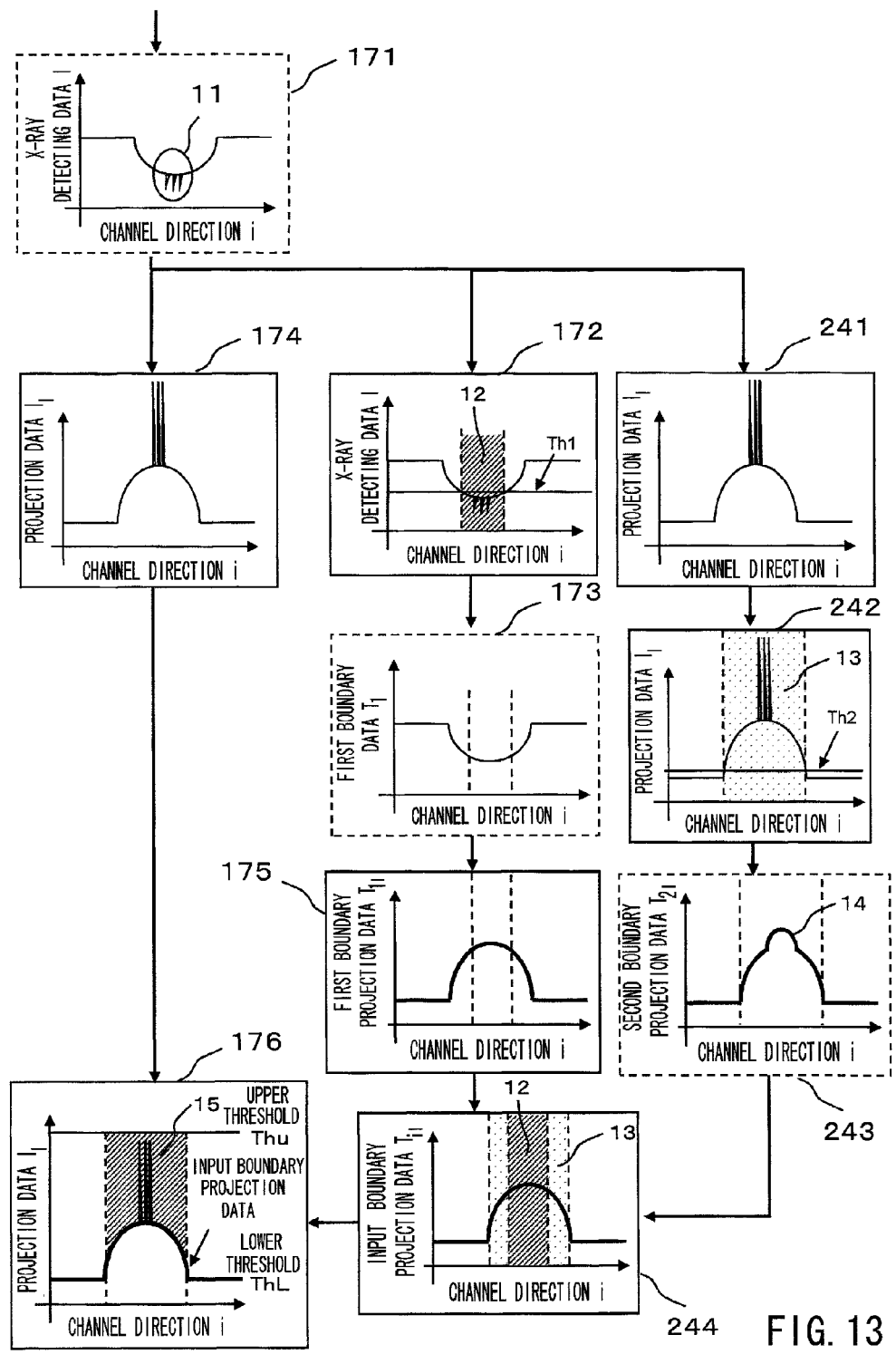
FIG. 13 illustrates a flow of the processing of the adaptive filter unit 135a and the data obtained at each process in the second embodiment.

FIG. 12 shows a flow of the processing in the present embodiment and each state of data during the processing is illustrated in FIG. 13. In FIG. 12, the steps 162 to 167 are executed in the similar manner as the processing of the decision unit of processing range 151 and the decision unit of processing function 152 being explained in the first embodiment with reference to FIG. 5. Consequently, the data 172, 173, and the first boundary projection data $T_{1l}$ 175 as shown in FIG. 13 are obtained. In the flow of FIG. 12, the steps 231 to 234 are executed to generate the second boundary projection data $T_{2l}$. Furthermore, the step 235 in FIG. 12 is executed to set the boundary projection data by selecting the first or the second boundary projection data for each channel. Accordingly, the data 241, data 242, data 243, and data 244 as shown in FIG. 13 are obtained.

The steps 231 to 234 will be explained specifically. In the step 231, as illustrated by the data 241 in FIG. 13, a publicly known air calibration processing is performed on the X-ray detecting data I of the data 171, and thereafter, the X-ray detecting data I is subjected to the logarithmic conversion according to the formula (5) of the first embodiment. Then, the projection data $I_l$ (i, j, k) of the attenuation coefficient (data 241 in FIG. 13) is acquired (step 232).

Next, in the step 233, as illustrated by the data 242 in FIG. 13, the projection data $I_l$ is smoothed in the range 13 where the projection $I_l$ satisfies equal to or more than a threshold Th2, thereby generating the second boundary data $T_{2l}$ (i, j, k). By way of example, the smoothing processing uses a method of convolution with the filter function on the X-ray detecting data. Consequently, in the step 234, as illustrated by the data 243 in FIG. 13, the noise component 11 can be reduced by smoothing, but at the center part 14, the noise is not completely removed and certain noise resides, since the smoothing processing is performed on the noise that has been intensified by the logarithmic conversion.

In the step 233, the threshold Th2 is used to limit the filter application range 13, whereby it is possible to reduce the calculation amount and the memory amount in the step 234 and the steps subsequent thereto as shown in FIG. 12.

It is to be noted that the threshold Th2 used in the step 233 is decided by using the formula (2) from the relationship 191; B=μ·l expressing the product of the attenuation coefficient and the path length of transmission for the rate A=I/I$_o$ of X-ray photon count, as shown in FIG. 8 of the first embodiment. It is to be noted that in the formula (2), the value C is decided according to the X-ray irradiation condition such as the imaged region and the filter condition such as the mode of the adaptive filter, with the aim of making the filter application range 13 to be larger than the filter application range 12 that is set by the threshold Th1. In the present embodiment, it is assumed that C=−0.5, and accordingly the threshold Th2 of the step 233 is set to 2.0 [cm$^{-1}$]. Consequently, when the projection data $I_l$ satisfies equal to or more than the threshold Th2, the area with a low X-ray dose after passing through the subject (the filter application range 13) is determined as an area for the smoothing by the adaptive filter. Since the area outside the filter application range 13 is an area with a high X-ray dose, the smoothing is not performed thereon.

In the next step 235, the first boundary projection data $T_{1l}$ obtained by smoothing the X-ray detecting data and subsequently performing logarithmic conversion thereon, and the second boundary projection data $T_{2l}$ obtained by logarithmic conversion on the X-ray detecting data and subsequently performing smoothing processing thereon are integrated, whereby the input boundary projection data $T_{il}$ (i, j, k) is determined. Here, the term "integrated" means that either the first boundary projection data $T_{1l}$ and the second boundary projection data $T_{2l}$ is selected for each channel (i, j, k).

Here, as a reference of the selection from the first boundary projection data $T_{1l}$ and the second boundary projection data $T_{2l}$, as expressed by the formula 12 and 13, a variation relative to an adjacent channel is calculated as to those data items by differential processing or the like, and the boundary projection data with smaller variation is selected as the boundary projection data for the channel (i, j, k).

$$T_{il} = T_{1l} \quad \frac{dT_{1l}}{di} < \frac{dT_{2l}}{di} \qquad \text{Formula 12}$$

$$T_{il} = T_{2l} \quad \frac{dT_{1l}}{di} > \frac{dT_{2l}}{di} \qquad \text{Formula 13}$$

Consequently, according to the variation of the first and the second boundary projection data, any one of the boundary projection data is selected to be used as the threshold, and therefore, the degree (weight δ) of smoothing can be changed. Therefore, it is possible to achieve an appropriate smoothing effect. When the first boundary projection data and the second boundary projection data are selected according to the formulas (12) and (13), as illustrated by the data 244 as shown in FIG. 13, the first boundary projection data $T_{1l}$ is mostly selected in the range 12 around the center of the channel, and the second boundary projection data $T_{2l}$ is mostly selected in the range 13 outside the range 12, as the boundary projection data $T_{il}$ (data 244 in FIG. 13).

The boundary projection data $T_{il}$ being obtained is used as the threshold ThL, and according to the formulas (6) to (9) of the first embodiment, smoothing processing is performed on the projection data $I_l$, thereby obtaining the smoothed projection data $I_l$ 176.

In the present embodiment, it is configured such that either the first boundary projection data $T_{1l}$ or the second boundary projection data $T_{2l}$ is used selectively for each channel (i, j, k). Since the first boundary projection data $T_{1l}$ is generated by smoothing before the logarithmic conversion, there is a possibility that noise is excessively reduced and this may deteriorate information of the subject, if only the first boundary projection data $T_{1l}$ is used. However, selective usage with the second boundary projection data $T_{2l}$ may prevent such possibility. On the other hand, since the second boundary projection data $T_{2l}$ is generated by smoothing after the logarithmic conversion, a noise component may be significantly intensified by the logarithmic conversion, resulting in that the noise component may reside at the center part 14 of the second boundary projection data $T_{2l}$. Consequently, there is a possibility that a value of the second boundary projection data $T_{2l}$ at the center part 14 becomes larger, failing in completely eliminating the noise. In the present embodiment, such possibility may be prevented by using the first boundary projection data and the second boundary projection data selectively. According the selective use of the first boundary projection data and the second boundary projection data for each channel (i, j, k), the degree of smoothing is switched, and it is possible to achieve smoothing which effectively eliminates noise without deteriorating the subject information.

It is to be noted that in the present embodiment, the first boundary projection data or the second boundary projection data is selected for each channel according to the formulas (12) and (13). However, this is not a limited configuration and areas where first boundary projection data and the second boundary projection data are applied respectively may be determined from the X-ray detecting data and/or the projection data. By way of example, the first boundary projection data $T_{1l}$ may be used for the filter application range 12 equal to or less than the threshold Th1 that is determined in the step 162 of FIG. 12. The second boundary projection data $T_{2l}$ may be used for the filter application range 13 equal to or more than the threshold Th2 that is determined in the step 233. Accordingly, for the area where the X-ray detecting data changes steeply due to noise components and the like (range 12), the first boundary projection data $T_{1l}$ is used to perform the smoothing intensively. On the other hand, for the area where the subject information is required to be held (range 13), the second boundary projection data $T_{2l}$ is used to perform the smoothing weakly. Consequently, deterioration of spatial resolution is suppressed while the noise is reduced.

In order to verify the effectiveness of the adaptive filter of the proposed method, a simulation was performed. For the simulation, a quantum noise included in the image being actually imaged and a system noise such as a circuit were taken into account. The phantom was assumed as a human body abdomen, having an oval shape as illustrated by the images 251 and 252 in FIGS. 14(a) and (b), and it was made of acryl with an attenuation rate similar to a living body. On the right periphery of the phantom, there was provided a high attenuated phantom 253 including three lines in one set, each line having different line distance, so as to evaluate the spatial resolution. Enlarged images 254 and 255 according to different methods respectively are shown, and the distances between the line pair were set to 0.95 [lp/mm] and 1.00 [lp/mm]. The X-ray tube voltage and the quantity of X-ray tube current were set to 80 kV, 50 mAs, respectively. It is to be noted, however, that the X-ray tube voltage and the quantity of X-ray tube current are not limited to those values of the present embodiment.

Figure 14:
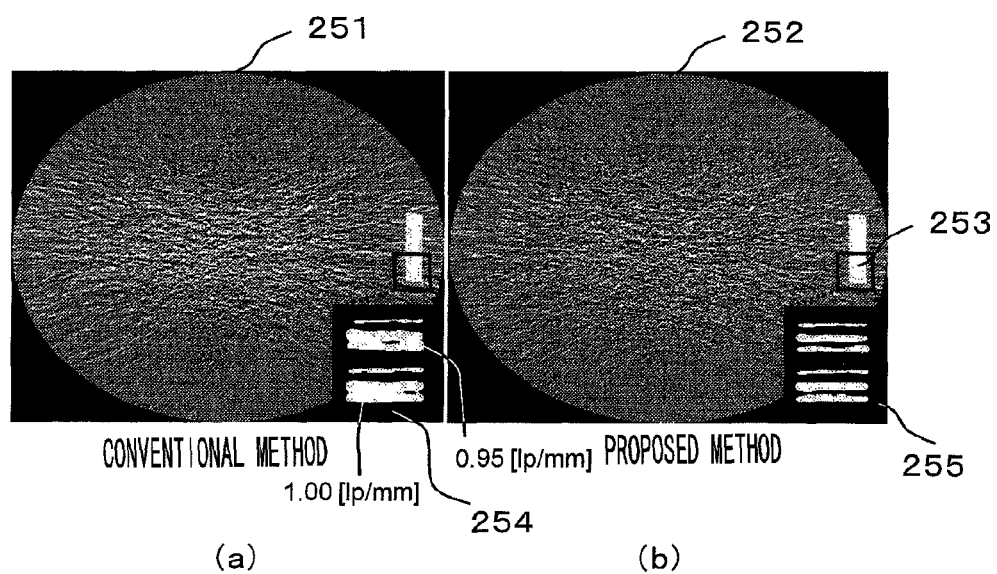
FIG. 14(a) illustrates a CT image of phantom and an effect of the adaptive filter according to a conventional method.
FIG. 14(b) illustrates a CT image of phantom and an effect of the adaptive filter according to the second embodiment.

As a result of this simulation, as shown in FIG. 14(a), streak artifacts occurred in the horizontal direction according to general convolution being a conventional method. However, as a result of applying the proposed method as shown in FIG. 14(b), the streak artifacts were reduced. According to the conventional method as shown in FIG. 14(a), the smoothing was performed intensively on the periphery, the spatial resolution was deteriorated, and therefore disabling the line pair to be identified. However, in the proposed method, all of the line pairs of the three lines, having distance of 0.95 [lp/mm] and 1.00 [lp/mm], were identifiable as shown in FIG. 14(b). As shown in FIGS. 14(a) and (b), it is possible for the proposed method to suppress the deterioration of the spatial resolution, and reduce the artifacts, compared to the conventional adaptive filter.

Figure 15:
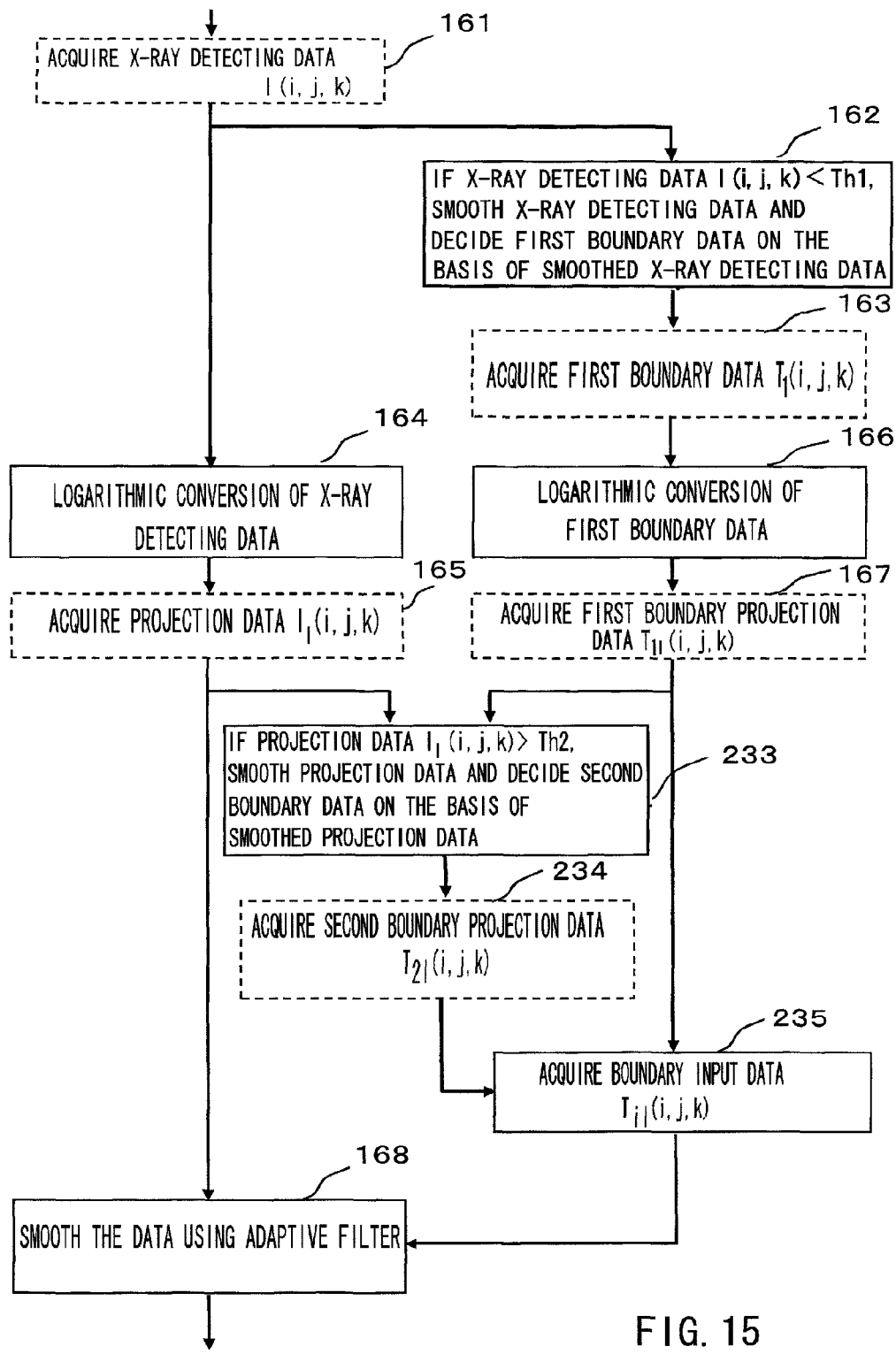
FIG. 15 is a flowchart for explaining a flow of the processing of the adaptive filter unit 135a with the purpose to reduce a calculation amount and a memory amount according to the second embodiment.

In the present embodiment, as shown in the steps 231 to 232 of FIG. 12, the entire X-ray detecting data is subjected to the logarithmic conversion. However, as shown in FIG. 15, it is alternatively possible that after the first boundary data area (range 12) is set in the steps 161 to 167, the logarithmic conversion is performed on the range other than the first boundary data area, and thereafter the projection data is smoothed to generate the second boundary projection data (step 233 and step 234). With this configuration, the range of channel on which the arithmetic operation for generating the second boundary projection data is performed is limited to the outside of the range 12, and therefore, it is possible to reduce the calculation amount and the memory amount.

In the present embodiment, by way of example, the area (range 12) for smoothing by using the first boundary projection data is decided from the X-ray detecting data. However, this is not the only example and it is possible to decide the area from the projection data that is obtained by subjecting the X-ray detecting data to the logarithmic conversion. For example, the threshold E is determined from the attenuation coefficient of the projection data, and it is assumed E=1.0 [cm$^{-1}$].

In the present embodiment, by way of example, the areas for smoothing (the range 12 and the range 13) are determined from the relationship (B=μ·l) 191 expressing the product of the attenuation coefficient and the path length of transmission for the rate A=I/I$_o$ of the X-ray photon count. However, this is not the only example, and the area for smoothing may be determined, assuming an arbitrary attenuation coefficient as the threshold F. For example, smoothing is performed assuming that F is 2.0, and also assuming that the area with the attenuation coefficient equal to or more than F indicates an area with a low X-ray dose.

Third Embodiment

In the third embodiment, noise is detected on a reconstructed image obtained from the projection data that has been corrected by the adaptive filter according to the first or the second embodiment. If the detected noise value is large, the condition is changed and smoothing by the adaptive filter is performed again, thereby reducing the artifacts in the CT image. In the following, the proposed method will be explained in detail.

Figure 16:
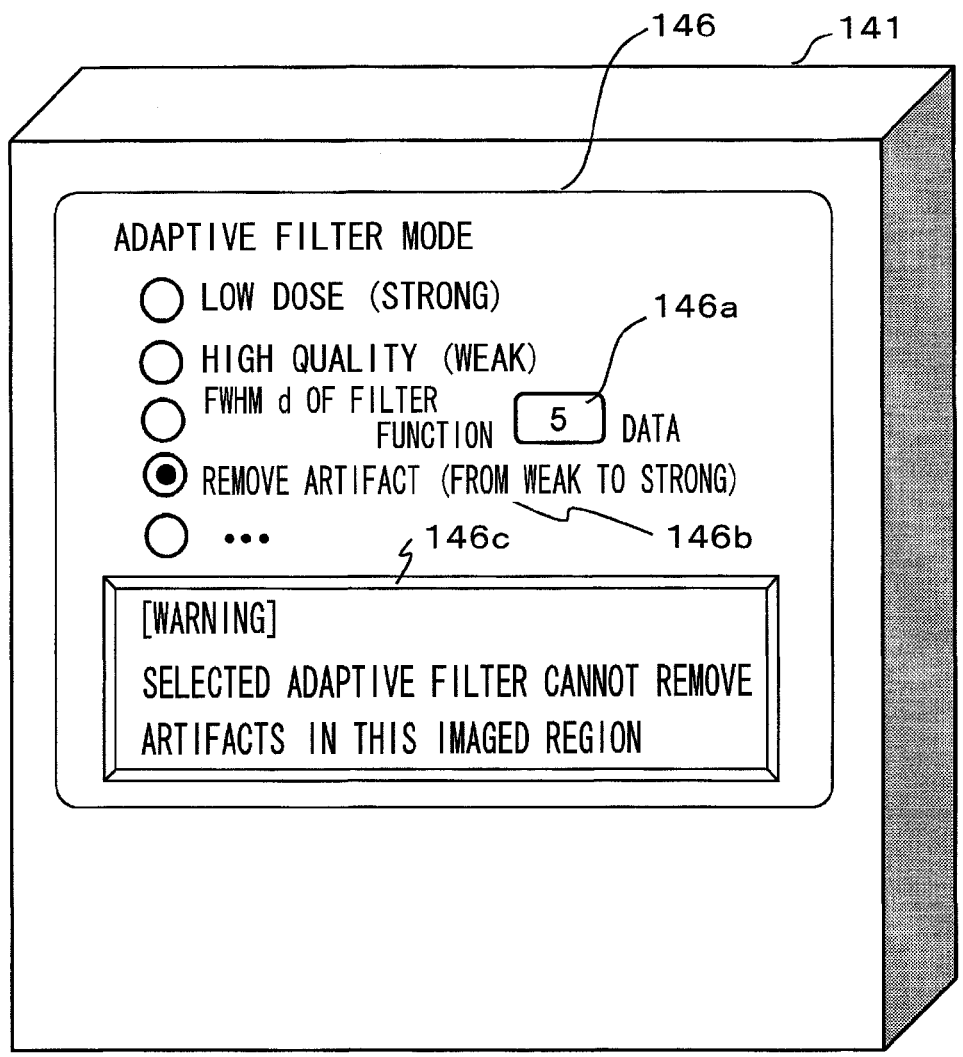
FIG. 16 illustrates a monitor screen 141 for setting the imaging condition, of the imaging condition input unit in a third embodiment and in a fourth embodiment of the proposed method.

In the third embodiment, as shown in FIG. 16, a selecting unit of removing artifact mode 146b is added to the selecting unit of adaptive filter mode 146, on the monitor screen 141 for setting imaging condition as shown in FIG. 3, thereby enabling a selection of effect of removing artifact from several levels, from weak to strong.

Figure 17:
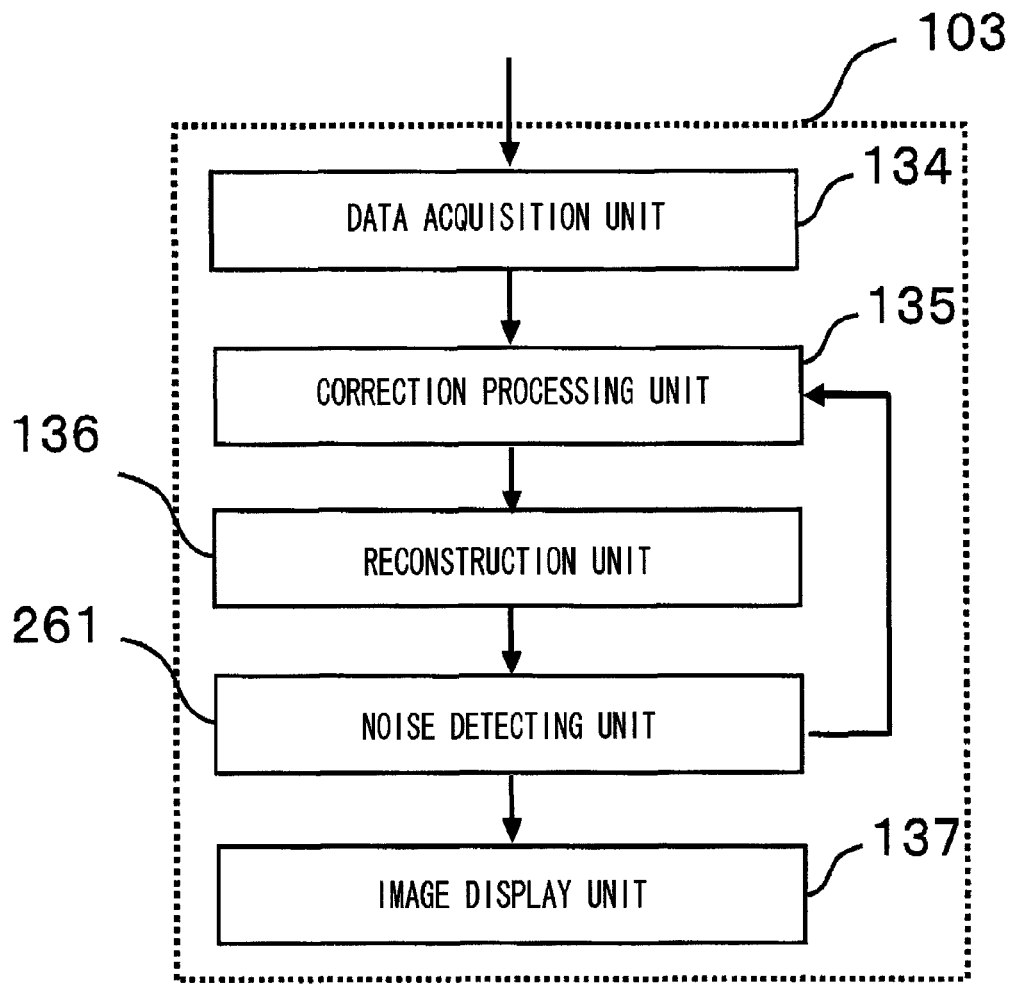
FIG. 17 is a block diagram showing functions of an image calculation unit 103 and a flow of the operation in the third embodiment.

The image calculation unit 103 has a configuration similar to FIG. 2, but as shown in FIG. 17, it additionally incorporates a noise detecting unit 261, and a circuit for giving a feedback to the correction processing unit 135 regarding a detected result.

Figure 18:
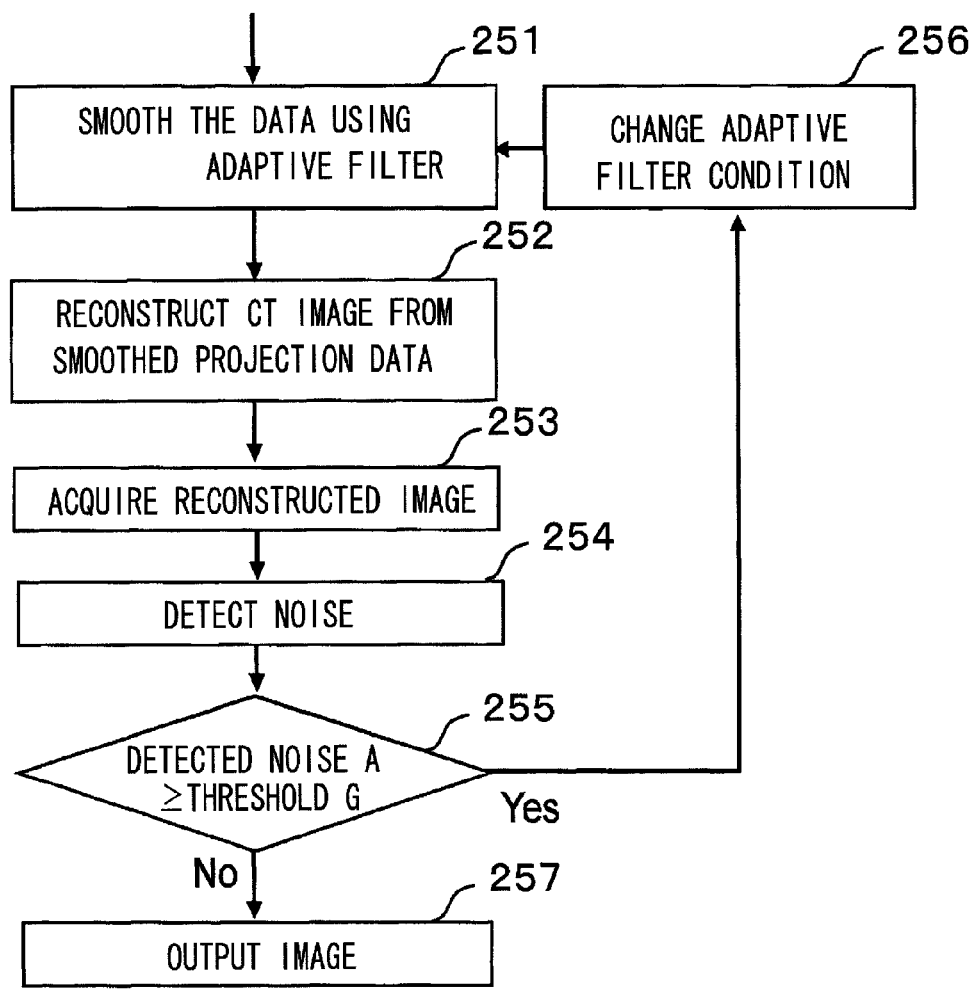
FIG. 18 is a flowchart for explaining a flow of the smoothing processing by the adaptive filter unit 135a in the third embodiment.

With reference to FIG. 17 and FIG. 18, a specific processing of the CT apparatus according to the third embodiment will be explained. In the correction processing unit 135, smoothing processing is performed with the use of the adaptive filter in the same manner as the first embodiment or the second embodiment (step 251). The reconstruction unit 136 performs the image reconstruction by using the projection data $I_l$ having been smoothed (step 252). Next, the noise detecting unit 261 acquires the reconstruction image from the reconstruction unit 136 (step 253), and by using a publicly known image processing technique such as a detecting line method, a noise value is detected (step 254). As a publicly known image processing technique, a method can be employed as one example, which subjects a predetermined area or the entire area of the image to the threshold processing, thereby selecting a line-shaped part (noise) from a white part, detects a maximum value, a standard deviation, or the like, of the signal values in the noise part, and assumes it as a noise value A.

When the noise value A being detected is equal to or larger than a predetermined threshold G, the noise detecting unit 261 gives feedback to the correction processing unit 135, and changes the condition of the adaptive filter (step 255, 256). A value of the threshold G is predefined for each level of the effect of removing artifact (from weak to strong) in the selecting unit of removing artifact mode 146b, and a threshold is employed, in association with the level that is selected by the operator from weak to strong. By way of example, when a maximum value of the noise is assumed as the noise value A, it is possible to configure setting that the threshold G=10.

In order to change the condition of the adaptive filter in the step 256, there is employed, for instance, a method for enlarging FWHM d of the filter function, or a method for lowering the entire values of the first boundary projection data and/or the second boundary projection data. A predetermined amount may be automatically set as the amount of change in values of FWHM d or the boundary projection data. It is further possible to configure such that a warning is displayed for the operator in the display 146c as shown in FIG. 16, and variation in values of the FWHM and the boundary projection data is accepted. Accordingly, in the step 251 after the feedback, an effect of smoothing by the adaptive filter is intensified, and smoothing processing is performed again on the projection data stored in the memory 120, HDD 122, and the like. The operations (steps 251 to 256) are repeated until the detected noise reaches less than the threshold G.

As thus described, in the third embodiment, it is possible to reduce the artifacts in the CT image to be equal to or less than a desired value.

Fourth Embodiment

In the fourth embodiment, a residual amount of artifact after applying the adaptive filter is estimated in advance, by using the X-ray irradiation condition such as the imaged region and the X-ray condition, and the filter processing condition, which are entered in the monitor screen 141 and the like for setting the imaging condition as shown in FIG. 3, and the like.

Measured data or simulation data according to clinical or phantom experiments is obtained in advance, and the residual amount of artifact is obtained as to each multiple combinations of the X-ray irradiation conditions and the filter conditions for each diameter and for each region of the subject, and then a database is constructed. The database being obtained is stored in the storage unit of filter parameters 154 within the adaptive filter unit 135a as shown in FIG. 4.

With this configuration, the correction processing unit 135 searches the database in the storage unit of filter parameters 154, for conditions that are close to the X-ray irradiation condition and the filter condition set by the operator in the monitor screen 141 for setting the imaging condition, and reads the residual amount of artifact matching the conditions. Consequently, before performing the actual imaging, it is possible to estimate the residual amount of artifact after smoothing.

As shown in the display 146c of FIG. 16, when the residual amount of artifact after smoothing is larger than the predetermined residual amount, the correction processing unit warns the operator that artifacts still reside since the adaptive filter condition is not appropriate for the inputted imaging condition. As described above, the proposed method relates to the X-ray CT apparatus, and handles an appropriate adaptive filter according to the inputted imaging condition, and consequently, deterioration in spatial resolution of a CT image can be suppressed and artifacts can be reduced, even with a small amount of calculation and a small amount of memory. Accordingly, reduction of artifacts is possible even in the imaging with a low dose, and low dose imaging becomes implementable.

DENOTATION OF REFERENCE NUMERALS

1 . . . X-RAY TUBE, 2 . . . X-RAY DETECTING UNIT, 3 . . . GANTRY, 4 . . . ROTATING PLATE, 5 . . . TABLE, 6 . . . SUBJECT, 7 . . . CIRCULAR APERTURE, 11 . . . NOISE COMPONENT, 12 . . . FILTER APPLICATION RANGE OF X-RAY DETECTING DATA, 13 . . . FILTER APPLICATION RANGE OF PROJECTION DATA, 14 . . . CENTRAL PART OF THE SECOND BOUNDARY PROJECTION DATA, 15 . . . APPLICATION RANGE OF ADAPTIVE FILTER, 101 . . . INPUT UNIT, 102 . . . IMAGING UNIT, 103 . . . IMAGE CALCULATION UNIT, 111 . . . KEYBOARD, 112 . . . MOUSE, 113 . . . MEMORY, 114 . . . CENTRAL PROCESSING UNIT, 115 . . . HDD, 116 . . . GANTRY CONTROLLER, 117 . . . X-RAY CONTROLLER, 118 . . . TABLE CONTROLLER, 119 . . . DAS, 120 . . . MEMORY, 121 . . . CENTRAL PROCESSING UNIT,

122 ... HDD, 123 ... MONITOR, 131 ... INPUT UNIT OF IMAGING CONDITION, 132 ... IMAGING CONTROL UNIT, 133 ... IMAGING EXECUTION UNIT, 134 ... DATA ACQUISITION UNIT, 135 ... CORRECTION PROCESSING UNIT, 135a ... ADAPTIVE FILTER UNIT, 136 ... RECONSTRUCTION UNIT, 137 ... IMAGE DISPLAY UNIT, 141 ... MONITOR SCREEN, 142 ... SELECT LIST OF IMAGED REGION, 143 ... IMAGING CONDITION, 144 ... SELECT LIST OF ADAPTIVE FILTER PROCESSING, 145 ... DIRECTION OF ADAPTIVE FILTER PROCESSING, 146 ... ADAPTIVE FILTER MODE, 151 ... DECISION UNIT OF PROCESSING RANGE, 152 ... DECISION UNIT OF PROCESSING FUNCTION, 153 ... EXECUTION UNIT OF PROCESSING FUNCTION, 154 ... STORAGE UNIT OF FILTER PARAMETERS, 181 ... PROJECTION DATA, 201 ... PROJECTION DATA OF PROJECTION ANGLE j' AND SLICE k', 202 ... FILTER FUNCTION, 203 ... SMOOTHED PROJECTION DATA, 251 ... RECONSTRUCTED IMAGE ACCORDING TO A CONVENTIONAL METHOD, 252 ... RECONSTRUCTED IMAGE ACCORDING TO THE PROPOSED METHOD, 253 ... HIGH ATTENUATED PHANTOM, 254 ... ENLARGED VIEW OF HIGH ATTENUATED PHANTOM ACCORDING TO THE CONVENTIONAL METHOD, 255 ... ENLARGED VIEW OF HIGH ATTENUATED PHANTOM ACCORDING TO THE PROPOSED METHOD, 261 ... NOISE DETECTING UNIT

What is claimed is:

1. An X-ray computed tomography (CT) apparatus, comprising:
   an X-ray irradiation unit for irradiating X-rays;
   an X-ray detecting unit for detecting the X-rays that have passed through a subject and generating X-ray detecting data;
   a calculation unit of projection data for subjecting the X-ray detecting data to logarithmic conversion and generating projection data;
   a filter processing unit for smoothing at least one of the X-ray detecting data and the projection data; and
   an image calculation unit for calculating from data acquired in the filter processing unit, a CT image which represents a distribution of X-ray attenuation coefficient,
   wherein the filter processing unit generates boundary data by using at least a part of the X-ray detecting data and the projection data, and performs smoothing processing on at least one of the X-ray detecting data and the projection data, using the boundary data as a threshold, and
   wherein the filter processing unit compares the X-ray detecting data with the boundary data, or the projection data with the boundary data, and sets a smoothing degree of smoothing processing according to a difference between the compared data.

2. The X-ray CT apparatus according to claim 1, wherein a comparison is made between the projection data and the boundary data, and the smoothing processing is not performed in an area where the projection data is smaller than the boundary data, whereas in an area where the projection data is equal to or larger than the boundary data, the smoothing processing is performed in accordance with a difference between the projection data and the boundary data.

3. The X-ray CT apparatus according to claim 1, wherein a comparison is made between the X-ray detecting data and the boundary data, and the smoothing processing is not performed in an area where the X-ray detecting data is larger than the boundary data, and in an area where the X-ray detecting data is equal to or smaller than the boundary data, the smoothing processing is performed in accordance with a difference between the X-ray detecting data and the boundary data.

4. The X-ray CT apparatus according to claim 1, wherein the filter processing unit generates the boundary data by performing the smoothing processing on the X-ray detecting data or the projection data.

5. The X-ray CT apparatus according to claim 4, wherein the filter processing unit sets an area of the X-ray detecting data, being equal to or less than a predetermined threshold, as a filter application range, and performs the smoothing processing on the X-ray detecting data within the filter application range, so as to generate the boundary data.

6. The X-ray CT apparatus according to claim 4, wherein the filter processing unit sets an area of the projection data, being equal to or more than a predetermined threshold, as a filter application range, and performs the smoothing processing on the projection data within the filter application range, so as to generate the boundary data.

7. The X-ray CT apparatus according to claim 1, wherein the filter processing unit performs the smoothing processing on the X-ray detecting data in an area of the X-ray detecting data, being equal to or less than a predetermined first threshold, and thereafter performs logarithmic conversion thereon so as to generate first boundary data, performs the smoothing processing on the projection data in an area being equal to or more than a predetermined second threshold so as to generate second boundary data, and performs the smoothing processing on the projection data, by selectively using either of the first boundary data and the second boundary data.

8. The X-ray CT apparatus according to claim 7, wherein the filter processing unit obtains a variation rate of the first boundary data and a variation rate of the second boundary data, and selects either data with a smaller variation rate.

9. The X-ray CT apparatus according to claim 8, wherein the filter processing unit obtains the variation rate with respect to a channel direction, and selects either one of the first boundary data and the second boundary data for each channel.

10. The X-ray CT apparatus according to claim 1, wherein the filter processing unit performs the smoothing processing on the X-ray detecting data in a first area of the X-ray detecting data, being equal to or less than a predetermined first threshold, and thereafter performs logarithmic conversion thereon so as to generate first boundary data, performs the smoothing processing on the projection data in a second area of the projection data, being outside area of the first area and equal to or more than a predetermined second threshold so as to generate second boundary data, and performs the smoothing processing on the projection data, by using the first boundary data for the first area and by using the second boundary data for the second area.

11. The X-ray CT apparatus according to claim 10, wherein the first area is an area where the X-ray dose after passing through the subject is lower than the dose in the second area.

12. The X-ray CT apparatus according to claim 1, further comprising:
   a noise detecting unit for detecting a noise value of the CT image, wherein the filter processing unit changes a condition of smoothing processing, when the noise value detected by the noise detecting unit is larger than a predetermined value.

13. The X-ray CT apparatus according to claim 12, wherein when the noise value detected by the noise detecting unit is larger than the predetermined value, the filter processing unit changes the condition of smoothing processing by changing a value of the boundary data.

14. The X-ray CT apparatus according to claim 1, further comprising:
   an input unit for accepting an X-ray irradiation condition of the X-ray irradiation unit, a processing condition of the filter processing unit, and a region of the subject;
   a storage unit for storing a residual amount of artifact which is obtained in advance with respect to each of the X-ray irradiation condition, the processing condition of the filter processing unit, and the region of the subject; and
   an artifact estimation unit for reading the residual amount of artifact from the storage unit, in association with information of the X-ray irradiation condition, the processing condition of the filter processing unit, and the region of the subject, the information being accepted by the input unit,
   wherein when the residual amount of artifact is larger than a predetermined value, the artifact estimation unit sends a notice to an operator.

15. The X-ray CT apparatus according to claim 14, wherein when the residual amount of artifact is larger than the predetermined value, the filter processing unit changes a condition of smoothing processing.

* * * * *